(12) United States Patent
Heitsch et al.

(10) Patent No.: US 6,511,989 B2
(45) Date of Patent: Jan. 28, 2003

(54) ACYLAMINOALKYL-SUBSTITUTED BENZENESULFONAMIDE DERIVATIVES, THEIR PREPARATION, THEIR USE AND PHARMACEUTICAL PREPARATIONS COMPRISING THEM

(75) Inventors: Holger Heitsch, Mainz-Kastel (DE); Heinrich Christian Englert, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/985,366

(22) Filed: Nov. 2, 2001

(65) Prior Publication Data

US 2002/0123494 A1 Sep. 5, 2002

(30) Foreign Application Priority Data

Nov. 3, 2000 (DE) .......................................... 100 54 481

(51) Int. Cl.$^7$ ........................ A61K 31/47; C07D 215/14
(52) U.S. Cl. ........................ 514/311; 546/169; 564/23; 564/39; 564/40; 514/584; 514/592; 514/593
(58) Field of Search ................................ 514/311, 584, 514/592, 593; 546/169; 564/23, 39, 40

(56) References Cited

U.S. PATENT DOCUMENTS

| | | |
|---|---|---|
| 3,454,636 A | 7/1969 | Aumuller et al. |
| 3,507,961 A | 4/1970 | Weber et al. |
| 4,066,639 A | 1/1978 | Weber et al. |
| 5,476,850 A | 12/1995 | Englert et al. |
| 5,574,069 A | 11/1996 | Englert et al. |
| 5,652,268 A | 7/1997 | Englert et al. |
| 5,698,596 A | 12/1997 | Englert et al. |

FOREIGN PATENT DOCUMENTS

| | | |
|---|---|---|
| DE | 1443878 | 12/1968 |
| DE | 1518877 | 1/1969 |
| GB | 1080705 | 8/1967 |
| GB | 1116355 | 6/1968 |
| WO | WO 00/03978 | 1/2000 |
| WO | WO 00/15204 | 3/2000 |
| WO | WO 00/71513 A1 | 11/2000 |

OTHER PUBLICATIONS

Burger, Andrew J., et al., Short– and Long–Term Reproducibilty of Heart Rate Variability in Patients With Long–Standing Type I Diabetes Mellitus, The American Journal of Cardiology, 80:1198–1202 (1997).
Evans, David, A., et al., Synthesis of Diaryl Ethers through the Copper–Promoted Arylation of Phenols with Arylboronic Acids. An Expedient Synthesis of Thyroxine, Tetrahedron Letters, 39:2937–3940 (1998).
Inagaki, Nobuya, et al., Reconstitution of I$_{KATP}$: An Inward Rectifier Subunit Plus the Sulfonylurea Receptor, Science, 270:1166–1170 (1995).
Inagaki, Nobuya, et al., A Family of Sulfonylurea Receptors Determines the Pharmacological Properties of ATP–Sensitive K$^+$ Channels, Neuron, 16:1011–1017 (1996).
Kinugawa, Turo, et al., Altered Vagal and Sympathetic Control of Heart Rate in Left Ventricular Dysfunction and Heart Failure, Am. J. Physiol., 268:R310–R316 (1995).
Lawson, James W., Antiarrhythmic Activity of Some Isoquinoline Derivatives Determined by a Rapid Screening Procedure in the Mouse, The Journal of Pharmacology and Experimental Therapeutics, vol. 160, 1:22–31 (1968).
Rocca, P., et al., A New Convergent Synthesis of alpha–Substituted—beta—Carbolines, Tetrahedron, vol. 49, 16:3325–3342 (1993).
Schwartz, Peter. J., The ATRAMI Prospective Study: Implications for Risk Stratification after Myocardial Infarction, Cardiac Electrophysiology Review, 2:38–40 (1998).
Vanoli, Emilio, et al., Vagal Stimulation and Prevention of Sudden Death in Concsious Dogs With a Healed Myocardial Infarction, Circulation Research, vol. 58, 5:1471–1481 (1991).
Weichert, Andreas, et al., Palladium (0) Catalyzed Cross Coupling Reactions of Hindered, Double Activated Aryl Halides wth Organozinc Reagents—The Effect of Copper(I) Cocatalysis, Synlett, 473–474 (1996).
English–language Abstract for DE 1,443,878, Derwent World Patents Index.
English–language Abstract for DE 1,518,877, Derwent World Patents Index.

*Primary Examiner*—C. S. Aulakh
(74) *Attorney, Agent, or Firm*—Finnegan, Henderson, Farabow, Garrett & Dunner, LLP

(57) ABSTRACT

One embodiment of the present invention relates to acylaminoalkyl-substituted benzenesulfonamide derivatives of the formula (I),

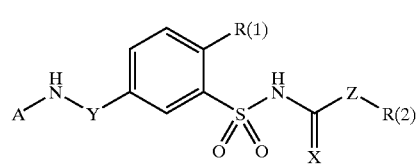

in which A, R(1), R(2), X, Y, and Z have the meanings indicated in the specification, and to pharmaceutically tolerable salts thereof. The compounds of the invention are valuable pharmaceutically active compounds that have, for example, an inhibitory action on ATP-sensitive potassium channels in the cardiac muscle and/or in the vagal cardiac nerve and are suitable, for example, for the treatment of disorders of the cardiovascular system such as coronary heart disease, arrhythmias, cardiac insufficiency, cardiomyopathies, decreased contractility of the heart or vagal dysfunction of the heart, or for the prevention of sudden cardiac death. The invention furthermore relates to processes for the preparation of the compounds of the formula (I) and pharmaceutically tolerable salts thereof, their use, and pharmaceutical preparations comprising them.

25 Claims, No Drawings

ACYLAMINOALKYL-SUBSTITUTED BENZENESULFONAMIDE DERIVATIVES, THEIR PREPARATION, THEIR USE AND PHARMACEUTICAL PREPARATIONS COMPRISING THEM

This application claims the benefit of the filing date of German Patent Application Number 10054481.9, filed on Nov. 3, 2000, which application is hereby incorporated by reference.

One embodiment of the present invention relates to acylaminoalkyl-substituted benzenesulfonamide derivatives of the formula (I),

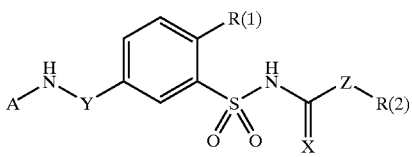

in which A, R(1), R(2), X, Y and Z have the meanings indicated below. The compounds of the formula (I) are valuable pharmaceutically active compounds that have, for example, an inhibitory action on ATP-sensitive potassium channels in the cardiac muscle and/or in the vagal cardiac nerve and are suitable, for example, for the treatment of disorders of the cardiovascular system such as coronary heart disease, arrhythmias, cardiac insufficiency, cardiomyopathies, decreased contractility of the heart or vagal dysfunction of the heart, or for the prevention of sudden cardiac death. Another embodiment of the invention relates to processes for the preparation of compounds of the formula (I), their use and pharmaceutical preparations comprising them.

For certain benzenesulfonylureas, a blood-sugar-lowering action has been described. A prototype of such blood-sugar-lowering sulfonylureas is glibenclamide, which is used therapeutically as an agent for the treatment of diabetes mellitus. Glibenclamide blocks ATP-sensitive potassium channels and is used in research as a tool for the exploration of potassium channels of this type. In addition to its blood-sugar-lowering action, glibenclamide has other actions that are attributed to the blockade of precisely these ATP-sensitive potassium channels but that hitherto can still not be used therapeutically. These include, for example, an anti-fibrillatory action on the heart. In the treatment of ventricular fibrillation or its early stages with glibenclamide however, the marked blood-sugar-lowering simultaneously produced by this substance would be undesirable or even dangerous, as it can further worsen the condition of the patient, so that glibenclamide is not suitable clinically as an antiarrhythmic.

Various patent documents, for example U.S. Pat. No. 5574069, U.S. Pat. No. 5698596, U.S. Pat. No. 5476850, U.S. Pat. No. 5652268 or WO-A-00/03978, disclose anti-fibrillatory benzenesulfonylureas and -thioureas having reduced blood-sugar-lowering action. WO-A-00/15204 describes the action of some of these compounds on the autonomic nervous system. The properties of these compounds, however, are still not satisfactory in various respects, and there is an ongoing need for compounds having a more favorable pharmacodynamic and pharmacokinetic property profile that are better suited, for example, for the treatment of a disturbed cardiac rhythm and its consequences such as sudden cardiac death or a weakened myocardial contractile force.

Various benzenesulfonylureas having an acylaminoalkyl substituent, in which the acyl group can also be derived, inter alia, from cinnamic acids, and the blood-sugar-lowering action of these compounds are disclosed in DE-A-1443878, U.S. Pat. No. 3454636, DE-A-1518877 and U.S. Pat. No. 4066639. The benzenesulfonylureas that are described in GB-A-1116355 are just so characterized by a blood-sugar-lowering action, among them some specific benzenesulfonylureas that contain a heteroarylacryloyl-aminoalkyl group in the para position to the sulfonylurea group. In WO-A-00/71513 (international patent application PCT/EP00/04091) certain cinnamoylaminoalkyl-substituted benzenesulfonamide derivatives are described, which are distinguished by a marked action on ATP-sensitive potassium channels in the heart. Further investigations showed that the benzenesulfonamide derivatives of the present invention, which contain acylaminoalkyl substituent in the meta position to the sulfonyl group, show a marked action on ATP-sensitive potassium channels of the cardiac muscle and/or of the vagal cardiac nerve, without having a marked action on pancreatic potassium channels and thus are valuable pharmaceutical active compounds, for example, for the treatment of disorders of the cardiovascular system.

Another embodiment of the present invention relates to compounds of the formula(l),

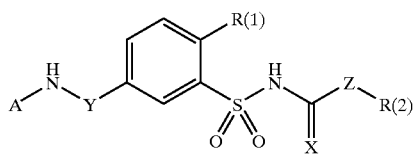

in which

R(1) is

1) $(C_1-C_4)$-alkyl; or

2) —O—$(C_1-C_4)$-alkyl which is unsubstituted or is substituted by 1, 2 or 3 fluorine atoms; or 3) —O—$(C_1-C_4)$-alkyl which is substituted by a substituent chosen from nitro, $((C_1-C_4)$-alkyl)carbonylamino, $(C_1-C_4)$-alkylamino, di$((C_1-C_4)$-alkyl)amino, hydroxycarbonyl, $((C_1-C_4)$-alkoxy)carbonyl, piperidin-1-yl, morpholin-4-yl, tetrahydrofuranyl, tetrahydropyranyl, phenyl, and phenoxy; where the phenyl group and the phenoxy group are unsubstituted or are substituted by one or two identical or different substituents chosen from halogen, $(C_1-C_4)$-alkyl, $(C_1-C_4)$-alkoxy, and trifluoromethyl; or 4) —O—$(C_1-C_4)$-alkyl-E(1)-$(C_1-C_4)$-alkyl-D(1), in which D(1) is hydrogen or —E(2)-$(C_1-C_4)$-alkyl-D(2), in which D(2) is hydrogen or —E(3)-$(C_1-C_4)$-alkyl, where E(1), E(2) and E(3), which are independent of one another and can be identical or different, are O, S, or NH; or 5) —O—$(C_1-C_4)$-alkyl-O—$(C_1-C_4)$-alkyl, which is substituted in the terminal alkoxy group by 1, 2 or 3 fluorine atoms; or 6) —O—$(C_2-C_4)$-alkenyl; or 7) —O-phenyl which is unsubstituted or is substituted by one or two identical or different substituents chosen from halogen, $(C_1-C_4)$-alkyl, $(C_1-C_4)$-alkoxy, and trifluoromethyl; or 8) halogen; or 9) phenyl, which is unsubstituted or is substituted by one or two identical or different substituents chosen from halogen, $(C_1-C_4)$-alkyl, $(C_1-C_4)$-alkoxy, —S(O)$_m$—$(C_1-C_4)$-alkyl, phenyl, amino, hydroxyl, nitro, trifluoromethyl, cyano, hydroxycarbonyl, carbamoyl, ((C$_1$–C$_4$)-alkoxy)carbonyl, and formyl; or 10) (C$_2$–C$_5$)-alkenyl, which is unsubstituted or is substituted by a substituent chosen from phenyl, cyano, hydroxycarbonyl, and ((C$_1$–C$_4$)-alkoxy)carbonyl; or 11) (C$_2$–C$_5$)-alkynyl, which is unsubstituted or is substituted by a substituent chosen from phenyl and (C$_1$–C$_4$)-alkoxy; or 12) 5-membered or 6-membered monocyclic heteroaryl having one or two identical or different ring heteroatoms chosen from oxygen, sulfur, and nitrogen; or 13) —S(O)$_m$-phenyl which is unsubstituted or is substituted by one or two identical or different substituents chosen from halogen, (C$_1$–C$_4$)-alkyl, (C$_1$–C$_4$)-alkoxy, and trifluoromethyl;

R(2) is hydrogen, (C$_1$–C$_6$)-alkyl or (C$_3$–C$_7$)-cycloalkyl, but is not hydrogen if Z is oxygen;

the residues R(3), which are all independent of one another and can be identical or different, are hydrogen or (C$_1$–C$_3$)-alkyl;

A is one of the following residues:

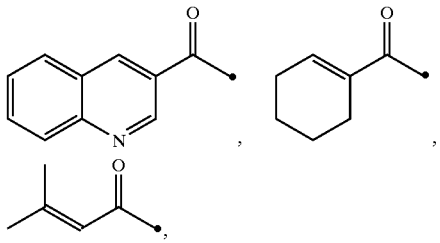

in which the free bond via which the residue is bonded to the amino group in the formula (I) is represented by the symbol —•;

X is oxygen or sulfur;

Y is —(CR(3)$_2$)$_2$)$_n$—;

Z is NH or oxygen;

m is 0, 1 or 2;

n is 1, 2, 3 or 4;

in all their stereoisomeric forms and mixtures thereof in all ratios, and their physiologically tolerable salts.

If groups, residues, substituents or variables can occur several times in the compounds of the formula (I), they can all independently of one another have the meanings indicated and can in each case be identical or different.

The term alkyl denotes straight-chain or branched saturated hydrocarbon residues. This also applies to groups derived therefrom such as, for example, alkoxy, alkoxycarbonyl or the residue —S(O)$_m$-alkyl. Examples of alkyl residues Include methyl, ethyl, n-propyl, isopropyl, n-butyl, sec-butyl, isobutyl, tert-butyl, n-pentyl, 1-methyl-butyl, isopentyl, neopentyl, tert-pentyl, n-hexyl or isohexyl. Examples of alkoxy include methoxy, ethoxy, propoxy such as n-propoxy and isopropoxy, butoxy such as n-butoxy, isobutoxy and tert-butoxy, etc. The same applies correspondingly to substituted alkyl residues, for example phenylalkyl residues, and to divalent alkyl residues (alkanediyl residues), in all of which the substituents or the bonds, via which the residues are bonded to the neighboring groups, can be situated in any desired positions. Examples of alkyl residues of this type, which are bonded to two neighboring groups, include —CH$_2$—, —CH(CH$_3$)—, —C(CH$_3$)$_2$—, —CH$_2$—CH$_2$—, —CH(CH$_3$)—CH$_2$—, —CH$_2$—CH(CH$_3$)—, —CH$_2$—CH$_2$—CH$_2$— or —CH$_2$—CH$_2$—CH$_2$—CH$_2$— all of which, inter alia, can represent the group Y or can be present in a group —O—(C$_1$–C$_4$)-alkyl which carries one substituent.

Alkenyl and alkynyl are straight-chain or branched, monounsaturated or polyunsaturated hydrocarbon residues, in which the double bonds and/or triple bonds can be situated in any desired positions. For example, the residues alkenyl and alkynyl may contain one double bond or one triple bond. Examples of alkenyl and alkynyl include vinyl, prop-2-enyl (allyl), prop-1-enyl, but-2-enyl, but-3-enyl, 3-methyl-but-2-enyl, pent-2,4-dienyl, ethynyl, prop-2-ynyl (propargyl), prop-1-ynyl, but-2-ynyl and but-3-ynyl. In substituted alkenyl residues and alkynyl residues the substituents can be situated in any desired positions.

Examples of cycloalkyl include cyclopropyl, cyclobutyl, cyclopentyl, cyclohexyl, and cycloheptyl all of which can also be substituted by one or more, for example one, two, three or four, identical or different (C$_1$–C$_4$)-alkyl residues, for example methyl residues.

Halogen is fluorine, chlorine, bromine, or iodine, for example, chlorine or fluorine.

In substituted phenyl residues the substituents can be situated in any desired positions. In monosubstituted phenyl residues the substituent can be situated in the 2-position, the 3-position, or the 4-position. In disubstituted phenyl residues the substituents can be situated in 2,3-position, 2,4-position, 2,5-position, 2,6-position, 3,4-position or 3,5-position. If a phenyl residue carries a further phenyl residue as a substituent, then this second phenyl residue can also be unsubstituted or can be substituted by the substituents indicated for the first phenyl residue, apart from a phenyl residue.

The heteroaryl residues, which are derived from monocyclic 5-membered or 6-membered aromatic ring systems, can also be regarded as residues derived from cyclopentadienyl or phenyl by replacement of one or two CH groups and/or CH$_2$ groups by S, O, N, NH (or N carrying a substituent such as, for example, N—CH$_3$), the aromatic ring system being retained or an aromatic ring system being formed. In addition to the one or two ring heteroatoms, they contain three to five ring carbon atoms. Examples of heteroaryl include furyl, thienyl, pyrrolyl, imidazolyl, pyrazolyl, 1,3-oxazolyl, 1,2-oxazolyl, 1,3-thiazolyl, 1,2-thiazolyl, pyridyl, pyrazinyl, pyrimidyl or pyridazinyl. A heteroaryl residue can be bonded via any ring carbon atom. For example, a thienyl residue can be present as a 2-thienyl residue or 3-thienyl residue, a furyl residue as a 2-furyl residue or 3-furyl residue, a pyridyl residue as a 2-pyridyl residue, 3-pyridyl residue or 4-pyridyl residue. A residue derived from 1,3-thiazole or from imidazole can be bonded via the 2-position, the 4-position, or the 5-position. Suitable nitrogen heterocycles can also be present as N-oxides or as quaternary salts with an anion derived from a physiologically tolerable acid as counter ion. Pyridine rings can thus also be present, for example, as pyridine N-oxides.

A tetrahydrofuranyl residue can be bonded via the 2-position or the 3-position, a tetrahydropyranyl residue via the 2-position, the 3-position or the 4-position. Examples of tetrahydrofuranyl and tetrahydropyranyl residues include tetrahydrofuran-2-yl and tetrahydropyran-2-yl.

Another embodiment of the present invention comprises all stereoisomeric forms of the compounds of the formula (I). Asymmetric centers present in the compounds of the formula (I) can all independently of one another have the S configuration or the R configuration. The invention includes all possible enantiomers and diastereomers, as well as mixtures of two or more stereoisomeric forms, for example mixtures of enantiomers and/or diastereomers, in all ratios. Enantiomers, for example, thus are a subject of the invention in enantiomerically pure form, as levorotatory as well as dextrorotatory antipode, in the form of the racemate and in the form of mixtures of the two enantiomeric forms in all ratios. In the presence of cis/trans isomerism or E/Z isomerism, the cis form, the trans form, the E form, the Z form and mixtures of these forms in all ratios are another subject of the invention. Individual stereoisomers can be prepared, if desired, by resolution of a mixture according to customary methods, for example by chromatography or crystallization, or by use of stereochemically uniform starting substances in the synthesis, or by stereoselective reactions. If appropriate, a derivatization can be carried out before separation of stereoisomers. The separation of a stereoisomer mixture can be carried out at the stage of the compounds of the formula (I) or at the stage of an intermediate in the course of the synthesis. The invention also comprises all tautomeric forms of the compounds of the formula (I).

Physiologically tolerable salts of the compounds of the formula (I) include nontoxic salts or pharmaceutically utilizable salts. They can contain inorganic or organic salt components. Such salts can be prepared, for example, from compounds of the formula (I) that contain one or more acidic groups, and nontoxic inorganic or organic bases. Possible bases include, for example, suitable alkali metal compounds or alkaline earth metal compounds, such as sodium hydroxide or potassium hydroxide, or ammonia or organic amino compounds or quaternary ammonium hydroxides. Reactions of compounds of the formula (I) with bases for the preparation of the salts are in general carried out according to customary procedures in a solvent or diluent. On account of the physiological and chemical stability, advantageous salts in the presence of acidic groups include in many cases sodium, potassium, magnesium or calcium salts or ammonium salts that can carry one or more organic residues on the nitrogen. Salt formation on the nitrogen atom of the benzenesulfonamide group in this case leads to compounds of the formula (II),

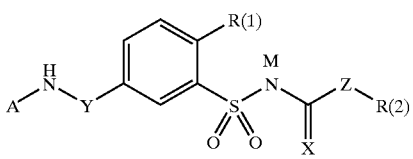

II in which A, R(1), R(2), X, Y, and Z have the meanings indicated above and the cation M, for example, is an alkali metal ion or an equivalent of an alkaline earth metal ion, for example the sodium, potassium, magnesium, or calcium ion, or the unsubstituted ammonium ion or an ammonium ion having one or more organic residues. An ammonium ion representing M can, for example, also be the cation that is obtained from an amino acid, for instance a basic amino acid such as, for example, lysine or arginine, by protonation.

Compounds of the formula (I) that contain one or more basic, i.e. protonatable, groups, can be present and can be used according to the invention in the form of their acid addition salts with physiologically tolerable inorganic or organic acids, for example as salts with hydrogen chloride, phosphoric acid, sulfuric acid or organic carboxylic acids or sulfonic acids such as, for example, p-toluenesulfonic acid, acetic acid, tartaric acid, benzoic acid, fumaric acid, maleic acid, citric acid etc. Acid addition salts can also be obtained from the compounds of the formula (I) according to customary processes known to the person skilled in the art, for example by combination with an organic or inorganic acid in a solvent or diluent. If the compounds of the formula (I) simultaneously contain acidic and basic groups in the molecule, the present invention also comprises internal salts or betaines (zwitterions), in addition to the salt forms described. The present invention also comprises all salts of the compounds of the formula (I) that, because of low physiological tolerability, are not directly suitable for use in pharmaceuticals but can be used, for example, as intermediates for chemical reactions or for the preparation of physiologically tolerable salts, for example by anion exchange or cation exchange.

The present invention furthermore comprises all solvates of compounds of the formula (I), for example hydrates or adducts with alcohols, and also derivatives of the compounds of the formula (I) such as, for example, esters and amides of acid groups, and prodrugs and active metabolites of compounds of the formula (I).

In one embodiment of the present invention, the acyl residue A is a quinoline-3-carbonyl residue. The residue A—NH— contained in the respective compounds, which is bonded to the group Y in the formula (I), can be designated, for example, as a 3-quinolinecarboxamido residue or a quinoline-3-carbonylamino residue. In a further embodiment of the present invention, the acyl residue A is a 1-cyclohex-1-enecarbonyl residue. The residue A—NH— contained in the respective compounds, which is bonded to the group Y in the formula I, can be designated, for example, as a 1-cyclohex-1-enecarbonylamino residue or a 1-cyclohex-1-enecarboxamido residue (or also as a cyclohex-1-enecarboxamido residue). In a further embodiment of the present invention, the acyl residue A is a 3-methylbut-2-enoyl residue. The residue A—NH— contained in the respective compounds, which is bonded to the group Y in the formula I, can be designated, for example, as a 3-methylbut-2-eneamido residue or a 3-methylbut-2-enoylamino residue (or also as 3,3-dimethylacryloylamino residue).

In one embodiment of the invention, in compounds of the formula (I) Z is oxygen and X is oxygen.

Y may be the residue —(CR(3)$_2$)$_n$— in which the residues R(3) are hydrogen or methyl, for example, hydrogen. n may be 2 or 3, for example, 2. An example of the group Y is the group —CH$_2$—CH$_2$—.

Z may be NH. Examples of compounds of the formula (I) include the benzenesulfonamide derivatives of the formula (Ia),

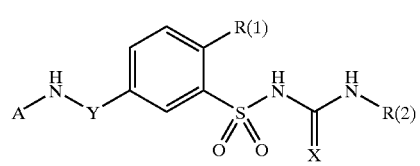

Ia in all their stereoisomeric forms and mixtures thereof in all ratios, and their physiologically tolerable salts. A subgroup of these compounds is formed by the benzenesulfonylthiourea derivatives of the formula (Ib),

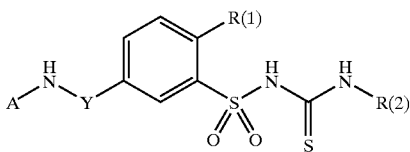

Ib in all their stereoisomeric forms and mixtures thereof in all ratios, and their physiologically tolerable salts, another subgroup is composed by the benzenesulfonylurea derivatives of the formula (Ic),

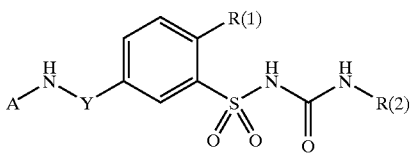

Ic in all their stereoisomeric forms and mixtures thereof in all ratios, and their physiologically tolerable salts. In the formulae (Ia), (Ib), and (Ic) the residues A, R(1), R(2), X and Y have the meanings indicated above. Another subgroup of the compounds according to the invention is formed by compounds of the formula (I) in which X is oxygen, Z is NH, and R(2) is methyl.

Examples of a ($C_1$–$C_4$)-alkyl residue representing R(1) include methyl, ethyl, and isopropyl.

An unsubstituted —O—($C_1$–$C_4$)-alkyl residue representing R(1) may include, for example, one of the residues methoxy, ethoxy, and propoxy for example methoxy or ethoxy. The alkyl group in a substituted —O—($C_1$–$C_4$)-alkyl residue representing R(1) may include, for example, a methyl group or an ethyl group that is substituted in the 2-position. A fluorine-substituted —O—($C_1$–$C_4$)-alkyl residue representing R(1) may include, for example, one of the residues trifluoromethoxy, 2-fluoroethoxy and 2,2,2-trifluoroethoxy, for example trifluoromethoxy. A substituted —O—($C_1$–$C_4$)-alkyl residue representing R(1), that carries a substituent other than fluorine atoms, may carry, for example, one of the substituents (($C_1$–$C_4$)-alkyl) carbonylamino, ($C_1$–$C_4$)-alkylamino, di(($C_1$–$C_4$)-alkyl) amino, piperidin-1-yl, morpholin4-yl, tetrahydrofuranyl, tetrahydropyranyl, phenoxy, and phenyl, for example morpholin-4-yl, tetrahydrofuranyl, tetrahydropyranyl, phenoxy, and phenyl, including tetrahydrofuranyl, tetrahydropyranyl, and phenyl, where the phenyl group and the phenoxy group can in each case be unsubstituted or substituted as indicated, for example unsubstituted. Examples of —O—($C_1$–$C_4$)-alkyl residues that carry a substituent other than fluorine atoms include tetrahydrofuran-2-ylmethoxy, tetrahydropyran-2-ylmethoxy, 2-(morpholin4-yl)ethoxy, 2-phenoxyethoxy, benzyloxy and 2-phenylethoxy, for example tetrahydrofuran-2-ylmethoxy, tetrahydropyran-2-ylmethoxy and benzyloxy.

In one embodiment of the invention, in the residue —O—($C_1$–$C_4$)-alkyl-E(1)-($C_1$–$C_4$)-alkyl-D(1) representing R(1), the groups E(1), E(2) and E(3) that can be present therein are oxygen. D(1) may be, for example, hydrogen. If D(1) has a meaning other than hydrogen, D(2) may be, for example, hydrogen. Examples of the residue —O—($C_1$–$C_4$)-alkyl-E(1)-($C_1$–$C_4$)-alkyl-D(1) include —O—($C_1$–$C_4$)-alkyl-O—($C_1$–$C_4$)-alkyl and —O—($C_1$–$C_4$)-alkyl-O—($C_1$–$C_4$)-alkyl-O—($C_1$–$C_4$)-alkyl, for instance O—($C_1$–$C_4$)-alkyl-O—($C_1$–$C_4$)-alkyl, such as 2-methoxyethoxy, 2-ethoxyethoxy, and 2-(2-methoxyethoxy)ethoxy, for example 2-methoxyethoxy and 2-ethoxyethoxy.

In the residue —O—($C_1$–$C_4$)-alkyl-O—($C_1$–$C_4$)-alkyl representing R(1) in which the terminal alkoxy group, i.e. the alkoxy group that is not directly bonded to the benzene ring in the formula (I), is substituted by fluorine atoms, the fluorine-substituted alkoxy group may be one of the groups trifluoromethoxy and 2,2,2-trifluoroethoxy. Examples of a fluorine-substituted —O—($C_1$–$C_4$)-alkyl-O—($C_1$–$C_4$)-alkyl residue representing R(1) include —O—($C_1$–$C_4$)-alkyl-O—$CF_3$ or —O—($C_1$–$C_4$)-alkyl-O—$CH_2$—$CF_3$, for example 2-(trifluoromethoxy)ethoxy or 2-(2,2,2-trifluoroethoxy)ethoxy.

An example of a residue —O—($C_2$–$C_4$)-alkenyl representing R(1) may be allyloxy.

A residue —O-phenyl representing R(1) may be, for example, unsubstituted or monosubstituted phenoxy, for example, phenoxy that is unsubstituted or substituted in the 4-position, including unsubstituted phenoxy, 4-methylphenoxy, 4-methoxyphenoxy, 4-fluorophenoxy or 4-trifluoromethylphenoxy.

Halogen representing R(1) may be, for example, bromine or iodine.

A phenyl residue representing R(1) may be, for example, unsubstituted or monosubstituted phenyl, including phenyl that is unsubstituted or substituted in the 4-position, for instance, phenyl, 4-methylphenyl, 4-methoxyphenyl, 4-fluorophenyl, or 4-trifluoromethylphenyl, for example, unsubstituted phenyl.

A residue ($C_2$–$C_5$)-alkenyl representing R(1) may be, for example, allyl.

A residue ($C_2$–$C_5$)-alkynyl representing R(1) may be, for example, ethynyl.

A heteroaryl residue representing R(1) may contain, for example, one ring heteroatom, and may be for instance, a pyridyl residue, thienyl residue or furyl residue, including the residues 2-pyridyl, 3-pyridyl, 2-thienyl and 2-furyl.

A residue —S(O)$_m$-phenyl representing R(1) may be, for example, unsubstituted or monosubstituted —S(O)$_m$-phenyl, for instance unsubstituted —S(O)$_m$-phenyl such as the unsubstituted residue —S-phenyl.

m may be, for example, 0 or 2, for instance 0.

In one embodiment of the invention R(1) is 1) methyl, ethyl, or isopropyl; or 2) methoxy, ethoxy, propoxy, trifluoromethoxy, 2-fluoroethoxy, or 2,2,2-trifluoroethoxy; or 3) tetrahydrofuran-2-ylmethoxy, tetrahydropyran-2-ylmethoxy, 2-(morpholin-4-yl)ethoxy, 2-phenoxyethoxy, benzyloxy, or 2-phenylethoxy; or 4) 2-methoxyethoxy, or 2-ethoxyethoxy; or 5) 2-(trifluoromethoxy)ethoxy, or 2-(2,2,2-trifluoroethoxy)ethoxy; or 6) allyloxy; or 7) phenoxy, 4-fluorophenoxy, 4-methylphenoxy, 4-methoxyphenoxy, or 4-trifluoromethylphenoxy; or 8) bromine or iodine; or 9) phenyl, 4-methylphenyl, 4-methoxyphenyl, 4-fluorophenyl, or 4-trifluoromethylphenyl; or 10) allyl; or 11) ethynyl; or 12) furyl, thienyl, or pyridyl; or 13) —S-phenyl.

In another embodiment of the invention R(1) includes those residues that are bonded via an oxygen atom to the benzene ring carrying the group R(1), and optionally substituted phenyl residue or heteroaryl residues. For example, R(1) may be one of the residues methoxy, ethoxy, trifluoromethoxy, 2-methoxyethoxy, 2-ethoxyethoxy, 2-(trifluoromethoxy)ethoxy, 2-(2,2,2-trifluoroethoxy) ethoxy, tetrahydrofuran-2-ylmethoxy, tetrahydropyran-2-ylmethoxy, or benzyloxy.

If Z is NH, R(2) may be, for example, hydrogen, $(C_1-C_4)$-alkyl or cyclohexyl, including $(C_1-C_4)$-alkyl or cyclohexyl, such as methyl, ethyl, isopropyl, or cyclohexyl, for example methyl, ethyl or isopropyl. A specific subgroup of compounds of the formula (I) in which Z is NH is formed by compounds in which R(2) is hydrogen or methyl. If Z is oxygen, R(2) may be, for example, $(C_1-C_4)$-alkyl. In one embodiment of the invention R2 is methyl.

More examples of the compounds of the formula (I) include those in which one or more of the residues present therein have the meanings exemplified above. All combinations of exemplified substituent definitions are also a subject of the present invention. Another embodiment of the invention includes all stereoisomeric forms of the compounds of the formula (I) exemplified above and mixtures thereof in all ratios, and their physiologically tolerable salts.

Thus, for example, a group of exemplified compounds may be formed by those compounds of the formula (I) in which Z is NH, X is sulfur and R(2) is methyl, and the other residues have the general or exemplified meanings indicated above, in all their stereoisomeric forms and mixtures thereof in all ratios, and their physiologically tolerable salts.

Another subgroup of the compounds of the invention is formed by those compounds of the formula (I) in which Y is —CH$_2$—CH$_2$—;

R(2) is methyl, ethyl, isopropyl or cyclohexyl;

and R(1), A, X and Z have the general or exemplified meanings indicated above, in all their stereoisomeric forms and mixtures thereof in all ratios, and their physiologically tolerable salts. Examples of more subgroups of the compounds of the invention include those compounds formed by compounds of the formula (I) in which Z is NH and/or X is sulfur. One more subgroup of the compounds of the invention is formed by compounds in which R(2) is methyl.

Another embodiment of the invention includes compounds of the formula (I) in which R(1) is methoxy, ethoxy, 2-methoxyethoxy, 2-ethoxyethoxy, trifluoromethoxy, 2-(trifluoromethoxy)ethoxy, 2-(2,2,2-trifluoroethoxy)ethoxy, tetrahydrofuranylmethoxy, tetrahydropyranylmethoxy, or benzyloxy;

R(2) is methyl, ethyl, or isopropyl;

Z is NH;

and A, X and Y have the general or exemplified meanings indicated above, in all their stereoisomeric forms and mixtures thereof in all ratios, and their physiologically tolerable salts.

Another embodiment of the present invention relates to processes for the preparation of the compounds of the formula (I), which are illustrated below and according to which the compounds of to the invention are obtainable.

Compounds of the formula (I) in which X is sulfur and Z is NH, i.e. benzenesulfonylthioureas of the formula (Ib),

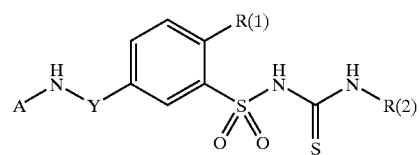

in which A, R(1), R(2), and Y have the abovementioned meanings, can be prepared, for example, by reacting benzenesulfonamides of the formula (III),

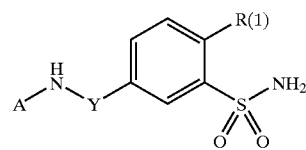

in which A, R(1), and Y have the abovementioned meanings, in an inert solvent or diluent with a base and with an R(2)-substituted isothiocyanate of the formula (IV)

in which R(2) has the meanings indicated above. Suitable bases include, for example, alkali metal or alkaline earth metal hydroxides, hydrides, amides or alkoxides, such as sodium hydroxide, potassium hydroxide, calcium hydroxide, sodium hydride, potassium hydride, calcium hydride, sodium amide, potassium amide, sodium methoxide, sodium ethoxide, potassium tert-butoxide, or quaternary ammonium hydroxides. The reaction of the compound of the formula (III) with the base can initially be carried out in a separate step and the resulting salt of the formula (V), can also be intermediately isolated, if desired.

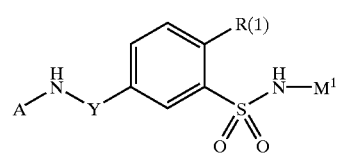

In the compounds of formula (V), A, R(1) and Y have the abovementioned meanings and the cation $M^1$ is an alkali metal ion, for example a sodium ion or potassium ion, or an equivalent of an alkaline earth metal ion, for example of a magnesium ion or calcium ion, or an ammonium ion which is inert under the reaction conditions, for example a quaternary ammonium ion. The salt of the formula (V), however, can also be produced in situ from the compound of the formula (III) and reacted directly with the isothiocyanate of the formula (IV). Suitable inert solvents for the reaction include, for example, ethers such as tetrahydrofuran (THF), dioxane, ethylene glycol dimethyl ether (DME) or diethylene glycol dimethyl ether (diglyme); ketones such as acetone or butanone, nitriles such as acetonitrile, nitro compounds such as nitromethane, esters such as ethyl acetate; amides such as dimethylformamide (DMF), N-methylpyrrolidone (NMP), or hexamethylphosphoric triamide (HMPT), sulfoxides such as dimethylsulfoxide (DMSO); or hydrocarbons such as benzene, toluene or xylenes. Furthermore, mixtures of these solvents with one another are also suitable. The reaction of the compound of the formula (III) or (V) with the compound of the formula (IV) may be, for example, carried out at temperatures from room temperature to about 150° C., including temperatures ranging from room temperature to about 100° C.

Compounds of the formula (I) in which X is oxygen and Z is NH, i.e. benzenesulfonylureas of the formula (Ic),

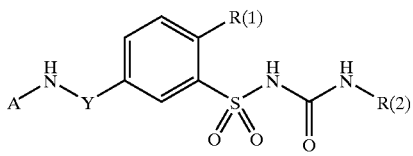

Ic in which A, R(1), R(2) and Y have the abovementioned meanings, can be prepared, for example, by reacting, analogously to the synthesis of the thiourea derivatives of the formula (Ib) described above, benzenesulfonamides of the formula (III) or their salts of the formula (V) in an inert solvent or diluent with a base and LAW OFFICES with an R(2)-substituted isocyanate of the formula (VI)

   VI in which R(2) has the meanings indicated above. The above illustrations of the reaction with isothiocyanates correspondingly apply to the reaction with the isocyanates.

Benzenesulfonylureas of the formula (Ic) can also be prepared from the benzenesulfonamides of the formula (III) or their salts of the formula (V) by reaction with R(2)-substituted 2,2,2-trichloroacetamides of the formula (VII),

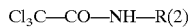   VII in which R(2) has the meanings indicated above, in the presence of a base in an inert, high-boiling solvent such as, for example, DMSO.

Benzenesulfonylureas of the formula (Ic) can also be prepared by means of a conversion reaction (desulfurization) from the corresponding benzenesulfonylthioureas of the formula (Ib). The replacement of the sulfur atom in the thiourea group of the compounds of the formula (Ib) by an oxygen atom can be carried out, for example, with the aid of oxides or salts of heavy metals or by use of oxidants such as hydrogen peroxide, sodium peroxide, or nitrous acid.

Benzenesulfonylureas and -thioureas of the formulae (Ic) and (Ib) can also be prepared by reaction of amines of the formula R(2)-NH$_2$. in which R(2) has the abovementioned meanings, with benzenesulfonyl isocyanates and isothiocyanates of the formula (VIII)

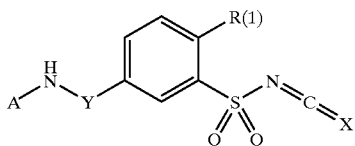

VIII in which A,R(1), X and Y have the abovementioned meanings. The sulfonyl isocyanates of the formula (VIII) (X=oxygen) can be obtained from the benzenesulfonamides of the formula (III) according to customary methods, for example using phosgene. The sulfonyl isothiocyanates of the formula (VIII) (X=sulfur) can be prepared by reaction of the sulfonamide of the formula III with alkali metal hydroxides and carbon disulfide in an organic solvent, such as DMF, DMSO, or NMP. The di-alkali metal salt of the sulfonyldithiocarbamic acid obtained here can be reacted in an inert solvent using a slight excess of phosgene or of a phosgene substitute such as triphosgene or using a chioroformic acid ester (2 equivalents) or using thionyl chloride. The solution of the sulfonyl iso(thio)cyanate of the formula (VIII) obtained can be reacted directly with the appropriately substituted amine of the formula R(2)-NH$_2$ or, if compounds of the formula (I) are to be prepared in which R(2) is hydrogen, can be reacted with ammonia.

Correspondingly, starting from benzenesulfonyl iso(thio)cyanates of the formula (VIII), by addition of alcohols of the formula R(2)-OH in which R(2) has the abovementioned meanings with the exception of hydrogen, compounds of the formula (I) can be prepared in which Z is oxygen, i.e. the benzenesulfonylurethane derivatives of the formula (Ih),

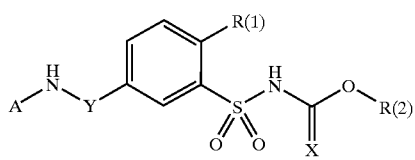

Ih in which A, R(1), R(2), X and Y have the abovementioned meanings, but R(2), as mentioned, is not hydrogen. Compounds of the formula (Ih) can also be prepared, for example, by reacting, analogously to the syntheses described above, benzenesulfonamides of the formula (III) or their salts of the formula (V) in an inert solvent, for example a high-boiling ether, with reactive carbonic acid derivatives, for example with chloroformic acid esters of the formula Cl—CO—OR(2) or pyrocarbonic acid diesters of the formula (R(2)O—C(=O))$_2$O in which R(2) has the abovementioned meanings with the exception of hydrogen. Starting from the compounds of the formula (Ih) in which X is oxygen, compounds of the formula Ic are in turn obtainable by reaction with the appropriate amine of the formula R(2)-NH$_2$ in an inert, high-boiling solvent, for example toluene, at temperatures up to the boiling point of the respective solvent.

The benzenesulfonamides of the formula (III) as the starting compounds for the processes for the synthesis of the benzenesulfonamide derivatives of the formula (I) can be prepared according to or analogously to known methods such as are described in the literature, for example in standard works like Houben-Weyl, Methoden der Organischen Chemie [Methods of Organic Chemistry], Georg Thieme Verlag, Stuttgart, and Organic Reactions, John Wiley & Sons, Inc., New York, and in the patent documents indicated above, the relevant parts of which are hereby incorporated by reference, if necessary with appropriate adjustment of the reaction conditions as is familiar to the person skilled in the art. Use can also be made in this case of variants that are known per se but not illustrated here in greater detail. In the synthesis, it may also be appropriate to temporarily block functional groups which would react in an undesired manner or give rise to side reactions by protective groups, or to employ them in the form of precursor groups which are only later converted into the desired groups. Strategies of this type are known to the person skilled in the art. Starting substances can, if desired, also be formed in situ in such a way that they are not isolated from the reaction mixture, but immediately reacted further.

Thus it is possible, for example, to react p-substituted benzene derivatives of the formula (IX),

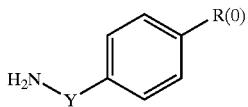

in which Y has the abovementioned meanings and R(0) is, for example, (C$_1$–C$_4$)-alkyl, (C$_1$–C$_4$)-alkoxy, bromine, or nitro, with trifluoroacetic anhydride in the presence of pyridine in an inert solvent such as, for example, THF to give compounds of the formula (X),

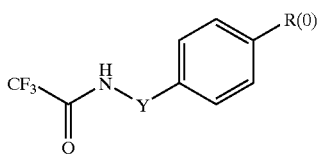

X in which Y and R(0) have the meanings indicated above.

Starting from the compounds of the formula (X) in which R(0) is nitro, it is possible by means of reduction of the nitro group using a reductant such as, for example, SnCl$_2$×2 H$_2$O in an inert solvent such as ethyl acetate, diazotization of the resulting amino group and subsequent reaction of the intermediate diazonium compound according to processes known per se, such as are described, for example, in Larock, Comprehensive Organic Transformations, VCH, 1989, for example by reaction with potassium iodide for the preparation of the iodo compounds, to obtain the corresponding p-halogen-substituted compounds of the formula (XI),

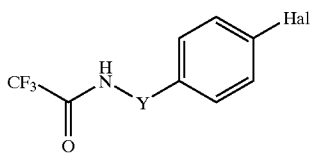

XI in which Y has the meanings indicated above and Hal is halogen.

The compounds of the formula (XI) and the compounds of the formula (X) in which R(0) is (C$_1$–C$_4$)-alkyl, (C$_1$–C$_4$)-alkoxy or bromine, which are collectively designated as compounds of the formula (XII),

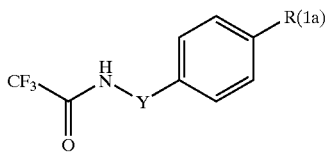

XII in which Y has the meanings indicated above and R(1a) is (C$_1$–C$_4$)-alkyl, (C$_1$–C$_4$)-alkoxy or halogen, can be converted in a known manner into the benzene sulfonamides of the formula (XIII),

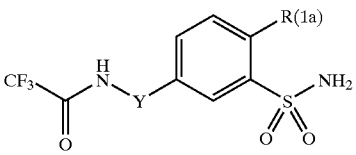

XIII in which Y and R(1a) have the meanings mentioned. The preparation of the sulfonamides of the formula (XIII) from the compounds of the formula (XII) can be carried out in one, two or more steps. Examples include processes in which the acylamines of the formula (XII) are first converted by means of electrophilic reagents in the presence or absence of inert solvents or diluents at temperatures from about –20° C. to about 120° C., including temperatures from about 0° C. to about 100° C., into the 2,5-substituted benzenesulfonic acids or their derivatives such as, for example, the sulfonic acid halides. For this, it is possible, for example, to carry out sulfonations using sulfuric acids or oleum, or halosulfonations using halosulfonic acids such as chlorosulfonic acid, or reactions with sulfuryl halides in the presence of anhydrous metal halides, or reactions with thionyl halides in the presence of anhydrous metal halides with subsequent oxidations, carried out in a known manner, to give sulfonyl chlorides. If sulfonic acids are the primary reaction products, these can be converted into sulfonic acid halides either directly or after treatment with amines such as, for example, triethylamine or pyridine, or with alkali metal or alkaline earth metal hydroxides or with other suitable bases, in a manner known per se by means of acid halides such as, for example, phosphorus trihalides, phosphorus pentahalides, thionyl halides or oxalyl halides. The conversion of the sulfonic acid derivatives into the sulfonamides of the formula (XIII) is carried out in a manner known from the literature. For example, sulfonyl chlorides are reacted with aqueous ammonia in an inert solvent such as, for example, acetone at temperatures from about 0° C. to about 100° C.

For the preparation of compounds of the formula (I) in which R(1) is (C$_1$–C$_4$)-alkyl, (C$_1$–C$_4$)-alkoxy or halogen, the compounds of the formula (XIII) can be converted by treatment with an acid such as, for example, hydrochloric acid or sulfuric acid, if appropriate with addition of a polar organic solvent such as methanol or ethanol, at temperatures from about 0° C. up to the boiling point of the solvent, into the compounds of the formula (XIV),

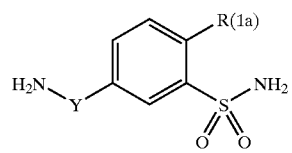

XIV in which R(1a) is (C$_1$–C$_4$)-alkyl, (C$_1$–C$_4$)-alkoxy or halogen and Y has the meaning indicated above.

For the preparation of compounds of the formula (I) in which R(1) is any of the other residues mentioned above, initially the sulfonamide group in suitable compounds of the formula (XIII) can be temporarily protected by conversion into the N—(N,N-dimethylaminomethylene)sulfonamide group. For example, starting from compounds of the formula (XIII) the dimethylaminomethylene compounds of the formula (XV),

XV

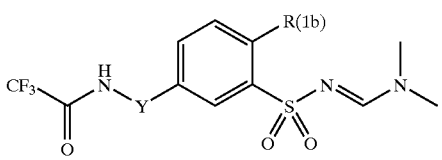

in which Y has the meanings mentioned and R(1b) is (C$_1$–C$_4$)-alkoxy, bromine or iodine, can be prepared by reacting the compounds of the formula (XIII), for example, with N,N-dimethylformamide dimethyl acetal or reacting them with N,N-dimethyl-formamide in the presence of dehydrating agents such as thionyl chloride, phosphorus oxychloride or phosphorus pentachloride.

The compounds of the formula (XV) in which R(1b) is (C$_1$–C$_4$)-alkoxy can then be converted by ether cleavage into the phenols of the formula (XVI)

XVI

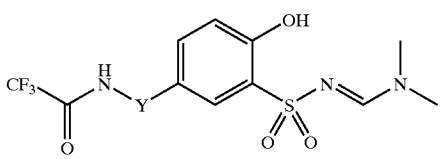

in which Y is as defined above. This ether cleavage is carried out, for example, by treatment of the compounds of the formula (XV) in which R(1b) is methoxy with acids or with Lewis acids such as boron trifluoride, boron trichloride, boron tribromide, aluminum trichloride, for instance boron tribromide, or their etherates, in an inert solvent such as, for example, dichloromethane.

The phenols of the formula (XVI) obtained can be converted into the compounds of the formula (XVII)

XVII

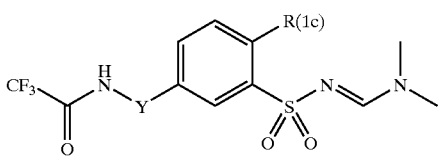

in which Y has the abovementioned meanings and R(1c) is one of the residues —O—(C$_1$–C$_4$)-alkyl-E(1)-(C$_1$–C$_4$)-alkyl-D(1), fluorine-substituted —O—(C$_1$–C$_4$)-alkyl-O—(C$_1$–C$_4$)-alkyl, substituted —O—(C$_1$–C$_4$)-alkyl, —O—(C$_2$–C$_4$)-alkenyl, or —O-phenyl. This conversion is carried out by means of an O-alkylation of the phenols of the formula (XVI) using appropriately substituted halogen compounds such as iodides or bromides or sulfonic acid esters such as methanesulfonic acid esters, p-toluenesulfonic acid esters or trifluoromethanesulfonic acid esters. The sulfonic acid esters are obtainable from the correspondingly substituted alcohols of the formula R(1c)-H according to standard processes, for example by using methanesulfonyl chloride in an inert solvent in the presence of a base such as potassium carbonate or cesium carbonate in the case of the methanesulfonic acid esters. For example, with (2-bromoethyl) methyl ether or benzyl bromide the compounds of the formula (XVII) and thus the final compounds of the formula (I) are obtained in which R(1c) and R(1), respectively, is 2-methoxyethoxy or benzyloxy. The O-alkylation is in general carried out in the presence of a base in an inert solvent at temperatures from about 0° C. up to the boiling point of the solvent according to processes known per se.

The preparation of compounds of the formula (XVII) in which R(1c) is —O-phenyl can be carried out by means of an O-arylation of the phenols of the formula (XVI) with phenylboronic acids, for example with phenylboronic acid or with substituted phenylboronic acids such as 4-methoxyphenylboronic acid, in the presence of copper catalysts, for example copper(II) acetate. Analogous reactions are described, for example, in Tetrahedron Lett. 39 (1998), 2937, the relevant disclosure of which is hereby incorporated by reference.

Starting from the compounds of the formula (XV) in which R(1b) is bromine or iodine, the compounds of the formula (XVIII)

XVIII

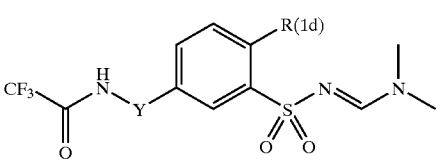

can be obtained in which Y has the indicated meanings and R(1d) is one of the residues (C$_1$–C$_4$)-alkyl, phenyl, (C$_2$–C$_5$)-alkenyl, (C$_2$–C$_5$)-alkynyl, heteroaryl or —S(O)$_m$-phenyl. The conversion into the compounds of the formula (XVIII) can be carried Gout by means of palladium-catalyzed Suzuki coupling using arylboronic acids, for example phenylboronic acid, 4-methoxyphenylboronic acid, or 4-methylthiophenylboronic acid, or heteroarylboronic acids, for example thienylboronic acid, or by means of Stille coupling using trialkylstannanes, for example tributylstannylfuran, trimethylstannylpyridine or ethinyltributylstannane. The Suzuki coupling is carried out in the presence of palladium (II) acetate and triphenylphosphine or tetrakis(triphenylphosphine)palladium and a base such as, for example, cesium carbonate or potassium carbonate. Corresponding reactions are described in the literature. The Stille coupling is carried out analogously to literature procedures using bis(triphenylphosphine)palladium(II) chloride as catalyst. The preparation of suitable stannanes is described, for example, in Tetrahedron 49 (1993) 3325, the relevant disclosure of which is hereby incorporated by reference. The preparation of compounds of the formula (XVIII) in which R(1d) is alkyl can be carried out by means of Pd(0)-catalyzed Nikishi-Kumada coupling of the compounds of the formula (XV) in which R(1b) is iodine with an appropriate organozinc derivative in the presence of 1,1'-bis(diphenylphosphino)ferrocene, palladium(II) acetate and copper(I) iodide as catalysts in an inert solvent. Corresponding couplings are described, for example, in Synlett 1996, 473, the relevant disclosure of which is hereby incorporated by reference.

Compounds of the formula (XVIII) in which R(1d) is —S-phenyl can be prepared, analogously to literature procedures, from the compounds of the formula (XV) in which R(1b) is iodine by means of a copper(I) iodide-catalyzed nucleophilic substitution reaction, using the sodium salt of the appropriate thiophenol. The thioether group introduced in this way, and just so thioether groups in other positions of the molecule of the formula (I) or of a synthetic intermediate, can be oxidized by standard processes to the sulfoxide group or to the sulfone group, for example by using a peracid such as m-chloroperbenzoic acid.

The subsequent removal of the dimethylaminomethylene group and of the trifluoroacetyl group functioning as a sulfonamide protective group and amino protective group, respectively, from the compounds of the formula (XVII) and (XVIII) then leads to the corresponding compounds having a $H_2N$—Y group and $H_2N$—$SO_2$ group which, together with the compounds of the formula (XIV), are represented by the formula (XIX),

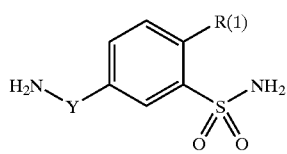

XIX in which Y and R(1) have the meanings indicated above for the formula(1). This removal of the protective groups can be carried out either under basic or under acidic conditions. This reaction may be carried out by treatment of the compounds of the formula (XVII) and (XVIII) in an inert solvent, for example an alcohol, with acids such as, for example, hydrochloric acid.

The benzenesulfonamides of the formula (XIX) are then acylated using carboxylic acid derivatives of the formula A—OH, in which the residue A has the meanings indicated above, to give the acylaminoalkyl-substituted benzenesulfonamides of the formula (III). The carboxylic acids of the formula A—OH are commercially available or can be prepared according to literature procedures. The acylation is in generally carried out by converting the carboxylic acid firstly into a reactive derivative, for example by reaction with N,N'-carbonyldiimidazole in an inert solvent such as, for example, THF, dioxane or DMF, and subsequent reaction with the amine of the formula(XIX), if appropriate in the presence of a base such as triethylamine or pyridine. As reactive derivatives of the carboxylic acids also the acid halides or the acid anhydrides, for example, can be used. The reactions in this case may be carried out at temperatures from about 0° C. up to the boiling point of the chosen solvent or diluent, including at room temperature. The acylation of the amines of the formula (XIX) using the carboxylic acids can also be carried out, for example, in the presence of condensing agents such as, for example, N,N'-dicyclohexylcarbodiimide, O-((cyano(ethoxycarbonyl)methylene)amino)-1,1,3,3-tetramethyluronium tetrafluoroborate (TOTU) or 1-benzotriazolyloxy-tripyrrolidinophosphonium hexafluorophosphate (PyBOP).

The steps described for the preparation of the compounds of the formula (I) can also be carried out in another sequence. Depending on the substituents to be introduced in the individual steps, one or another variant may be more advantageous. Thus, for example, the preparation of the compounds of the formula (III) in which R(1) is one of the residues $(C_1-C_4)$-alkyl, phenyl, $(C_2-C_5)$-alkenyl, $(C_2-C_5)$-alkynyl, heteroaryl or —$S(O)_m$-phenyl, can also be carried out in such a way that firstly a compound of the formula XIV in which R(1a) is iodine or bromine is converted by coupling with a carboxylic acid derivative and temporary protection of the sulfonamide group, as described above, into a compound of the formula (XX),

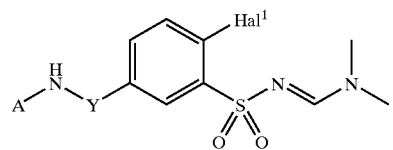

XX in which A and Y are as defined for formula (I) and $Hal^1$ is iodine or bromine. From the compound of the formula (XX), it is then possible by means of the Suzuki, Stille, or Nikishi-Kumada couplings described above using the appropriate abovementioned coupling components, to obtain the compounds of the formula (XXI),

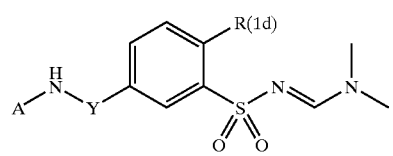

XXI in which A, R(1d) and Y have the meanings indicated above. The compounds of the formula (XXI) can then be converted into the compounds of the formula III by removal of the sulfonamide protective group according to the process described above.

The compounds of the invention inhibit ATP-sensitive potassium channels and influence the action potential of cells, for example, muscle cells. The compounds of the invention have a normalizing action on a disturbed action potential, such as is present, for example, in the case of ischemia, and are suitable, for example, for the treatment and prophylaxis of disorders of the cardiovascular system, including arrhythmias and their sequelae, for example of ventricular fibrillation or sudden cardiac death. The activity of the compounds of the invention can be demonstrated, for in the model described below, in which the action potential duration on the papillary muscle of the guinea pig is determined.

In addition to their action on ATP-sensitive potassium channels in the cardiac muscle cell, the compounds of the invention also have an action on the peripheral and/or the central autonomic nervous system. The compounds of the invention influence ATP-sensitive potassium channels of the vagal nervous system and have a stimulating action on the vagal nervous system, for example, a stimulating action on the vagal nervous system of the heart due to inhibition of ATP-sensitive potassium channels in the cardiac nerve.

In the ideal case, an optimum interaction, adapted to the particular situation, exists between the vagal (or parasympathetic) nervous system (=depressing nervous system) and the sympathetic nervous system (=stimulating nervous system). In the case of disease, however, this interaction may be disturbed and a dysfunction of the autonomic nervous system may be present, i.e. an inequilibrium may exist between the activity of the vagal nervous system and the activity of the sympathetic nervous system. Sympathovagal inequilibrium is understood in general as meaning a hyperactivity of the sympathetic (=stimulating) nervous system and/or a hypoactivity of the vagal (=depressing) nervous system, where the two parts of the nervous system can reciprocally influence one another. In particular, it is known that a hypoactivity of the vagal system can result in a hyperactivity of the sympathetic system. To avoid damage to cells or organs of the body due to overshooting biological or biochemical processes which are stimulated by an excessively high activity of the sympathetic nervous system, it is therefore attempted in such cases to compensate for a sympathovagal inequilibrium, for example to restore the normal vagal activity by eliminating a vagal dysfunction or hypoactivity.

Examples of diseases that can be treated by eliminating a vagal dysfunction and thus compensating for a harmful sympathovagal inequilibrium, are organic heart diseases such as coronary heart disease, cardiac insufficiency and cardiomyopathies. Damages to health that result from an inequilibrium of the autonomic nervous system when the dysfunction affects the heart include, for example, weakening of the myocardial contractile force and fatal cardiac arrhythmias. The importance of the autonomic nervous system for sudden cardiac death in heart diseases was described, for example, by P. J. Schwartz (The ATRAMI prospective study: implications for risk stratification after myocardial infarction; Cardiac Electrophysiology Review 2 (1998) 38) or T. Kinugawa et al. (Altered vagal and sympathetic control of heart rate in left ventricular dysfunction and heart failure; Am. J. Physiol. 37 (1995) R310). Experimental investigations with electrical stimulation of the cardiac vagus or stimulating analogs of the vagal transmitter acetylcholine, for example carbachol, confirm the protective action of a vagal activation against fatal cardiac arrhythmias (see, for example, E. Vanoli et al., Vagal stimulation and prevention of sudden death in conscious dogs with a healed myocardial infarction; Circ. Res. 68 (1991) 1471).

A sympathovagal inequilibrium, however, can also occur, for example, as a result of a metabolic disorder, for example of diabetes mellitus (see, for example, A. J. Burger et al., Short- and long-term reproducibility of heart rate variability in patients with long-standing type I diabetes mellitus; Am. J. Cardiol. 80 (1997) 1198). A hypoactivity of the vagal system can also temporarily occur, for example in the case of oxygen deficiency, for example oxygen deficiency of the heart, which leads to a reduced secretion of vagal neurotransmitters, for example of acetylcholine.

On account of the surprising ability of the compounds of the invention to abolish a hypoactivity of the vagal system or to restore the normal vagal activity, these compounds offer an efficient possibility of reducing, eliminating or preventing dysfunctions of the autonomic nervous system, including in the heart, and their sequelae such as, for example, the disease conditions mentioned. The efficacy of the compounds of the invention in the abolition of dysfunctions of the autonomic nervous system, for example of a vagal dysfunction of the heart, can be demonstrated in the model of chloroform-induced ventricular fibrillation in mice described below.

The compounds of the formula (I) and their physiologically tolerable salts can be used in animals, such as mammals, including humans, as pharmaceuticals on their own, in mixtures with one another or in the form of pharmaceutical preparations. Mammals in which the compounds of the invention can be used or tested are, for example, monkeys, dogs, mice, rats, rabbits, guinea pigs, cats and larger farm animals such as, for example, cattle and pigs. The invention therefore also relates to the compounds of the formula (I) and their physiologically tolerable salts and their prodrugs for use as pharmaceuticals, and pharmaceutical preparations (or pharmaceutical compositions) that contain an efficacious dose of at least one compound of the formula (I) and/or of a physiologically tolerable salt thereof and/or of a prodrug thereof as active constituent and a pharmaceutically tolerable carrier, i.e. one or more pharmaceutically acceptable vehicles and/or excipients (additives). The invention furthermore relates to the use of the compounds of the formula (I) and/or their physiologically tolerable salts and/or their prodrugs for the treatment, including the therapy and prophylaxis, of the syndromes mentioned above or below, to their use for the production of pharmaceuticals for the treatment, including therapy and prophylaxis, of the syndromes mentioned above or below, and to methods for the treatment, including the therapy and prophylaxis, of the syndromes mentioned above or below which comprise administering an efficacious amount of at least one compound of the formula (I) and/or a physiologically tolerable salt and/or a prodrug thereof.

The pharmaceutical preparations can be intended for enteral or parenteral use and may contain 0.5 to 90 percent by weight of at least one compound of the formula (I) and/or its physiologically tolerable salts and/or its prodrugs. The amount of active compound of the formula (I) and/or its physiologically tolerable salts and/or its prodrugs in the pharmaceutical preparations may range from about 0.2 to about 1000 mg, including from about 0.2 to about 500 mg, and from about 1 to about 300 mg, per dose unit. The pharmaceutical preparations can be prepared in a manner known per se. For this, the compounds of the formula (I) and/or their physiologically tolerable salts and/or their prodrugs are mixed with one or more solid or liquid vehicles and/or excipients and, if desired, with other pharmaceutical active compounds, for example pharmaceutical active compounds having cardiovascular activity such as, for example, calcium antagonists, ACE inhibitors or i-blockers, and brought into a suitable dose form and administration form, which can then be used as a pharmaceutical in human medicine or veterinary medicine.

Possible vehicles include organic and inorganic substances that are suitable, for example, for enteral, for example oral or rectal, administration, or for parenteral administration, for example by intravenous, intramuscular or subcutaneous injection or infusion, or for topical or percutaneous administration, and do not react in an undesired manner with the compounds of the invention. Examples of vehicles include water, vegetable oils, waxes, alcohols such as ethanol, propanediol or benzyl alcohols, glycerol, polyols, polyethylene glycols, polypropylene glycols, glyceryl triacetate, gelatin, carbohydrates such as lactose or starch, stearic acid and its salts such as magnesium stearate, talc, lanolin, petroleum jelly, or mixtures of two or more vehicles, for example mixtures of water with one or more organic solvents such as mixtures of water with alcohols. Examples of pharmaceutical forms for oral and rectal administration, include tablets, film-coated tablets, sugar-coated tablets, granules, hard and soft gelatin capsules, suppositories, solutions, including oily, alcoholic or aqueous solutions, syrups, juices, drops, suspensions, and emulsions. Examples of pharmaceutical forms for topical application include, ointments, creams, pastes, lotions, gels, sprays, foams, aerosols, solutions, and powders. As solvents for solutions including injection and infusion solutions, for example water or alcohols such as ethanol, isopropanol or 1,2-propanediol or their mixtures with one another or with water, among others, can be used. Further possible pharmaceutical forms include, for example, implants. The compounds of the formula (I) and their physiologically tolerable salts can also be lyophilized and the lyophilizates obtained used, for example, for the production of injection preparations. Liposomal preparations are also suitable, for example, for topical application. As examples of excipients (or additives) which can be present in the pharmaceutical preparations, glidants, preservatives, thickeners, stabilizers, disintegrants, wetting agents, agents for achieving depot effect, emulsifiers, salts (for example for influencing the osmotic pressure), buffer substances, colorants, flavorings, and aromatizers may be mentioned. If desired, pharmaceutical preparations can also contain one or more further active compounds and/or, for example, one or more vitamins.

On account of their ability to inhibit ATP-sensitive potassium channels, for example in the heart, and/or to decrease or to eliminate an inadequate function of the vagal nervous system and thereby a vagal dysfunction or a dysfunction of the autonomic nervous system, for example in the heart, the compounds of the formula (I) and their physiologically tolerable salts and prodrugs are valuable pharmaceutical active compounds that are suitable not only as antiarrhythmics and for the control and prevention of the sequelae of arrhythmias, but also for treatment and prophylaxis in other heart diseases or disorders of the cardiovascular system. Examples of such diseases that may be mentioned include cardiac insufficiency, cardiomyopathies, cardiac hypertrophy, coronary heart disease, angina pectoris, ischemia, and vagal dysfunction of the heart including, for example, vagal dysfunction of the heart in diabetes mellitus. The compounds of the invention can generally be employed in the treatment of diseases that are associated with a dysfunction of the autonomic nervous system or a hypoactivity or dysfunction of the vagal nervous system, for example in the heart, or are caused by such a dysfunction or in whose treatment an increase in or normalization of the activity of the vagal nervous system is desired. The compounds of the invention can also be employed in diseases that are characterized by oxygen deficiency conditions, in cerebral vascular disorders, and in dysfunctions of the autonomic nervous system, for example vagal dysfunction in the heart, which occur as a result of a metabolic disorder such as, for example, diabetes mellitus.

The compounds of the invention are used as antiarrhythmics for the treatment of cardiac arrhythmias of very different origin, including the prevention of sudden cardiac death due to arrhythmia. Examples of arrhythmic disorders of the heart include supraventricular arrhythmias such as, for example, atrial tachycardia, atrial flutters, or paroxysomal supraventricular arrhythmias, or ventricular arrhythmias such as ventricular extrasystoles, including life-threatening ventricular tachycardia and the particularly dangerous fatal ventricular fibrillation. They are suitable, for example, in those cases where arrhythmias are the result of constriction of a coronary vessel such as occur, for example, in angina pectoris or during acute cardiac infarcts or as a chronic result of a cardiac infarct. They are, therefore, suitable for the prevention of sudden cardiac death in post-infarct patients. Further syndromes in which arrhythmias of this type and/or sudden cardiac death due to arrhythmia play a part include, for example, cardiac insufficiency or cardiac hypertrophy as a result of chronically raised blood pressure.

Moreover, the compounds of the invention are able to positively influence decreased contractility of the heart and a weakened myocardial contractile force. This can be a disease-related decline in cardiac contractility, such as, for example, in cardiac insufficiency, but includes also acute cases such as heart failure in the case of shock. The compounds of the formula (I) and their physiologically tolerable salts are suitable for improving cardiac function. For example, in a heart transplantation, under the influence of the compounds of the invention, the heart can resume its capability faster and more reliably after the operation has taken place. The same applies to operations at on the heart that necessitate temporarily stopping cardiac activity by means of cardioplegic solutions.

Owing to the fact that the compounds of the invention, in addition to their direct cardiac action, i.e. the effect on the action potential of the cardiac muscle cells, also have an indirect action on the nervous system of the heart or on the parts of the nervous system acting on the heart, they can decrease or prevent undesirable sequelae emanating from the nervous system or mediated by the nervous system in the respective syndrome present. On account of this, further damage to health such as a weakening of the myocardial contractile force or in some cases fatal cardiac arrhythmias such as ventricular fibrillation can be reduced or avoided. Owing to the elimination or reduction of the dysfunction of the autonomic nervous system, the compounds of the invention have the effect that the weakened myocardial contractile force is normalized again and that the cardiac arrhythmias that can lead to sudden cardiac death do no longer develop. By selecting compounds of the invention having a suitable profile of action with respect to direct cardiac action (=direct effect on the action potential of the cardiac muscle cells and on account of this a direct effect on the contractile force and a direct antiarrhythmic effect) on the one hand and the action on the cardiac nerves on the other hand, it is efficiently possible with the aid of the compounds of the invention to favorably influence heart diseases. Depending on the syndrome present, it can also be advantageous in this case to employ compounds of the invention that have only a relatively slight direct cardiac effect and, on account of this, for example, have only a relatively slight direct effect on the contractile force of the heart or the formation of arrhythmias, but can improve or normalize the myocardial contractile force or the cardiac rhythm by means of the effect on the autonomic nervous system.

As used here, treatment includes therapy for a particular disease, such as treating cardiac insufficiency. In this respect, treatment can mean successfully eliminating the disease, reducing the effects associated with it, and/or reducing its severity. Treatment also includes prevention and prophylaxis of the onset of a disease by treating patients falling into a risk group or category for developing a particular disease or by treating patients after a successful treatment to prevent reoccurrence of the treated disease. Those skilled in the art can routinely identify patients likely to present with a disease, thereby qualifying as candidates for prevention therapy, because of factors such as diet, habits (e.g., smoking), family history for the disease, etc.

The dose of the compounds of the formula (I) or their physiologically tolerable salts depends, as usual, on the circumstances of the particular individual case and is adjusted by the person skilled in the art according to the usual rules and procedures. It depends, for example, on the specific compound of the invention administered, its potency and duration of action, on the nature and severity of the individual syndrome, on the sex, age, weight and on the individual responsiveness of the human or animal to be treated, on whether treatment is to be acute or prophylactic or on whether further active compounds are administered in addition to compounds of the invention. An effective amount of a compound of the invention is an amount sufficient to bring about a desired effect. For example, in the context of inhibition of ATP-sensitive potassium channels, an effective amount of a compound of the invention would constitute an amount sufficient to inhibit ATP-sensitive potassium channels.

Normally, In the case of administration to an adult weighing about 75 kg it is possible to manage with a dose that is about 0.1 mg to about 100 mg per kg per day, including doses from about 1 mg to about 10 mg per kg per day (in each case in mg per kg of body weight). The daily dose can be administered in the form of a single oral or parenteral dose or divided into a number of individual doses, for example two, three or four doses. The administration can also be carried out continuously. If acute cases of cardiac arrhythmias are treated, for example in an intensive care unit, parenteral administration, for example by injection or by intravenous continuous infusion, can be advantageous. A dose range in critical situations then may be from about 1 to about 100 mg per kg of body weight per day. Depending on individual behavior, it may be necessary to deviate upward or downward from the doses indicated.

Apart from being used as pharmaceutically active compounds in human medicine and veterinary medicine, the compounds of the invention can also be employed, for example, as auxiliaries for biochemical investigations or as a scientific tool when a respective effect on ion channels is intended, or for the isolation or characterization of potassium channels. They can also be used for diagnostic purposes, for example in in-vitro diagnoses of cell samples or tissue samples. The compounds of the formula (I) and their salts can furthermore be used as chemical intermediates for the production of further pharmaceutical active compounds.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the present specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The invention is illustrated by the examples below, without being restricted to these.

Abbreviations

| | |
|---|---|
| DCI | Desorption chemical ionization |
| DCM | Dichloromethane |
| DMF | Dimethylformamide |
| EA | Ethyl acetate |
| ESI | Electron spray ionization |
| FAB | Fast atom bombardment |
| M.p. | Melting point |
| h | Hour(s) |
| min | Minute(s) |
| MS | Mass spectrum |
| RT | Room temperature |
| THF | Tetrahydrofuran |

EXAMPLE 1

1-[5-(2-(3-Quinolinecarboxamido)ethyl)-2-methoxyphenylsulfonyl]-3-methyl-thiourea

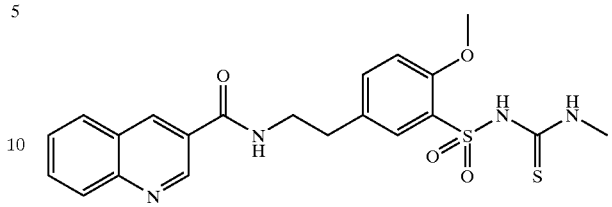

a) 2,2,2-Trifluoro-N-(2-(4-methoxyphenyl)ethyl)acetamide 32.2 ml (0.23 mol) of trifluoroacetic anhydride were added dropwise to a solution of 22.3 ml (0.15 mol) of 2-(4-methoxyphenyl)ethylamine and 24.7 ml (0.23 mol) of pyridine in 125 ml of absolute THF cooled to 5° C., and the resulting solution was stirred at RT for 3 h. The reaction solution was then poured onto 750 ml of ice, and the precipitate deposited was filtered off with suction and dried in a high vacuum at 40° C. 36.3 g of the title compound resulted as a beige solid.

M.p.: 74–77° C., $R_f$ (SiO$_2$, EA/toluene 1:4)=0.62; MS (ESI): m/z=248 [M+H]$^+$.

b) 2-Methoxy-5-(2-(2,2,2-trifluoroacetamido)ethyl) benzenesulfonamide 36.3 g (0.15 mol) of the compound of example 1a) were added in portions to 200 ml of chlorosulfonic acid and the resulting mixture was stirred at RT for 2 h. The reaction mixture was then added dropwise to about 1.5 of ice and the deposited precipitate was filtered off with suction. The precipitate was dissolved in 100 ml of acetone, and the solution was treated with 250 ml of concentrated ammonia solution with ice-cooling and stirring for 45 min. The reaction solution was then poured onto about 800 ml of ice. Filtering off the deposited precipitate with suction and drying it in a high vacuum yielded 30.4 g of the title compound as a pale yellow solid.

M.p.: 160–161° C.; $R_f$ (SiO$_2$, EA/heptane 4:1)=0.51; MS (DCI): m/z=327 [M+H]$^+$.

c) 5-(2-Aminoethyl)-2-methoxybenzenesulfonamide

A solution of 30.3 g (93.0 mmol) of the compound of example 1b) in 130 ml of 2N hydrochloric acid was heated to reflux for 12 h. The deposited precipitate was filtered off with suction, dissolved in 70 ml of water, and the pH of the resulting solution was adjusted to about 10 by addition of 2N sodium hydroxide solution. After brief warming to 100° C., the solution was cooled in an ice bath and the deposited precipitate was filtered off with suction. Drying of the precipitate in a high vacuum yielded 13.7 g of the title compound as a beige solid.

M.p.: 180–181° C.; $R_f$ (SiO$_2$, EA/heptane 4:1)=0.02; MS (ESI): m/z=231 [M+H]$^+$.

d) 5-(2-(3-Quinolinecarboxamido)ethyl)-2-methoxybenzenesulfonamide

A solution of 500 mg (2.89 mmol) of 3-quinolinecarboxylic acid in 20 ml of absolute THF was treated under an argon atmosphere with 515 mg (3.18 mmol) of N,N'-carbonyidiimidazole and stirred at RT for 3.5 h. The resulting solution was then treated successively with 1.4 ml of triethylamine and 770 mg (2.89 mmol) of the compound of example 1c) and stirred at RT for 20 h. The reaction solution was then poured onto 20 ml of 1N hydrochloric acid. The deposited precipitate was filtered off, washed with a little water and dried in a high vacuum. 508 mg of the title compound resulted as an amorphous beige solid.

$R_f$ (SiO$_2$, EA)=0.34; MS (ESI): m/z=386 [M+H]$^+$.

e) 1-[5-(2-(3-Quinolinecarboxamido)ethyl)-2-methoxyphenylsulfonyl]-3-methyl-thiourea A solution of 501 mg (1.30 mmol) of the compound of example 1d) and 178 mg (1.58 mmol) of potassium tert-butoxide in 9 ml of absolute DMF was stirred at 80° C. for 20 min. 1.61 ml of a 1M solution of methyl isothiocyanate in absolute DMF were added and the resulting solution was stirred at 80° C. for 1 h. The reaction solution was then poured onto 50 ml of 1N hydrochloric acid, and the deposited precipitate was filtered off with suction and washed repeatedly with water. Drying of the precipitate in a high vacuum yielded 188 mg of the title compound as a white solid.

M.p.: 85° C.; Rf (SiO2, EA)=0.50; MS (ESI): m/z=459 [M+H]$^+$.

EXAMPLE 2

1-[5-(2-(3-Quinolinecarboxamido)ethyl)-2-(2-methoxyethoxy)phonylsulfonyl]-3-methyl-thiourea

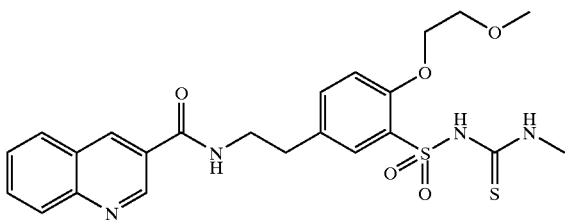

a) N-Dimethylaminomethylene-2-methoxy-5-(2-(2-2,2-trifluoroacetamido)ethyl)-benzenesulfonamide 30.2 g (92.6 mmol) of the compound of example 1b) were dissolved in 70 ml of absolute DMF, 14.0 ml (105.4 mmol) of dimethylformamide dimethyl acetal were added, and the resulting solution was stirred at RT for 3 h. It was concentrated to dryness, and the residue was stirred with 100 ml of water and 100 ml of 5% strength sodium hydrogensulfate solution. The crystalline precipitate obtained was washed repeatedly with water and then dried in a high vacuum. 29.6 g of the title compound resulted as a white solid.

M.p.: 143–144° C.; $R_f$ (SiO$_2$, EA)=0.25; MS (DCl): m/z=382 [M+H]$^+$.

b) N-Dimethylaminomethylene-2-hydroxy-5-(2-(2,2,2-trifluoroacetamido)ethyl)-benzenesulfonamide 100 ml of a 1M solution of boron tribromide in DCM were added dropwise over a period of 40 min at RT to a solution of 29.5 g (77.2 mmol) of the compound of example 2a) in 450 ml of DCM. After stirring at RT for 5 h, the reaction mixture was treated with 150 ml of methanol and then with about 2 l of diisopropyl ether. The deposited precipitate was filtered off with suction and dried in a high vacuum. 32.7 g of the hydrobromide salt of the title compound were obtained as a white solid.

M.p.: 160–161° C.; Rf (SiO2, EA)=0.52; MS (DCl): m/z=368 [M+H]$^+$.

c) N-Dimethylaminomethylene-2-(2-methoxyethoxy)-5-(2-(2,2,2-trifluoroacetamido)ethyl)benzenesulfonamide A mixture of 9.1 g (2.03 mmol) of the compound of example 2b) and 7.1 g (50.8 mmol) of potassium carbonate in 50 ml of absolute DMF was treated with 6.7 ml (71.7 mmol) of 2-bromoethyl methyl ether and stirred at 70° C. for 3 h. After adding a further 6.7 ml of 2-bromoethyl methyl ether and stirring at 70° C. for 2 h, the reaction solution was treated with about 300 ml of EA. The solution was washed with water and saturated sodium chloride solution, and the organic phase was dried over sodium sulfate and concentrated to dryness. The residual slightly yellow oil was purified by chromatography on silica gel using EA. Concentration of the product-containing fractions and drying in a high vacuum yielded 7.25 g of the title compound as a pale yellow solid.

M.p.: 134–136° C.; $R_f$ (SiO$_2$, EA)=0.35; MS (DCl): m/z=426 [M+H]$^+$.

d) 5-(2-Aminoethyl)-2-(2-methoxyethoxy)benzenesulfonamide

A solution of 7.24 g (17.0 mmol) of the compound of example 2c) in 100 ml of methanol and 100 ml of half-concentrated hydrochloric acid was heated to reflux for 8 h. About 40 ml of ethanol were then added to the reaction solution and the deposited precipitate was filtered off with suction. Washing of the precipitate with cold ethanol and drying in a high vacuum yielded 4.0 g of the hydrochloride salt of the title compound as a white solid.

M.p.: 230–233° C.; MS (DCl): m/z=275 [M+H]$^+$.

e) 5-(2-(3-Quinolinecarboxamido)ethyl)-2-(2-methoxyethoxy)benzenesulfonamide

According to the process described in example 1d), starting from 250 mg (0.80 mmol) of the compound of example 2d) and 167 mg (0.97 mmol) of 3-quinolinecarboxylic acid, 133 mg of the title compound were obtained as a white solid.

M.p.: 170° C.; $R_f$ (SiO$_2$, EA)=0.19; MS (ESI): m/z=430 [M+H]$^+$.

f) 1-[5-(2-(3-Quinolinecarboxamido)ethyl)-2-(2-methoxyethoxy)phenylsulfonyl]-3-methyl-thiourea According to the process described in example 1e), starting from 88 mg (0.20 mmol) of the compound of example 2e) and 224 µl (0.22 mmol) of a 1M solution of methyl isothiocyanate in absolute DMF, 61 mg of the title compound were obtained as a pale yellow amorphous solid after drying in a high vacuum.

$R_f$ (SiO$_2$, EA)=0.33; MS (ESI): m/z=503 [M+H]$^+$.

EXAMPLE 3

1-[5-(2-(3-Quinolinecarboxamido)ethyl)-2-(2-methoxyethoxy)phenylsulfonyl]-3-methyl-urea

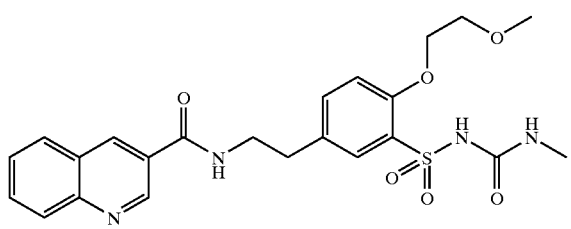

50 mg (0.10 mmol) of the compound of example 2f) were dissolved in 1 ml of 1N sodium hydroxide solution. 450 µl of a 35% strength aqueous hydrogen peroxide solution were added and the resulting solution was heated on the water bath for 30 min. The pH of the solution was then adjusted to 2 by addition of 2N hydrochloric acid. The deposited precipitate was filtered off with suction, washed with a little water and dried in a high vacuum. 20 mg of the title compound resulted as a pale yellow amorphous solid.

$R_f$ (SiO$_2$, EA)=0.08; MS (ESI): m/z=487 [M+H]$^+$.

EXAMPLE 4

1-[5-(2-(3-Quinolinecarboxamido)ethyl)-2-(2-(2,2,2-trifluoroethoxy)ethoxy)phenyl-sulfonyl]-3-methyl-thiourea

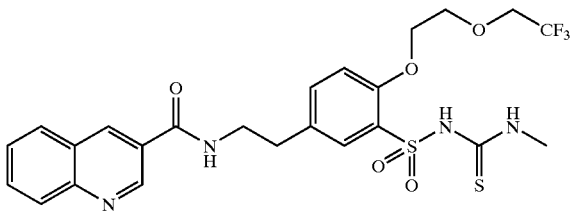

a) 2-(2,2,2-Trifluoroethoxy)ethanol

A mixture of 36 ml (0.50 mol) of 2,2,2-trifluoroethanol, 66 g (0.75 mol) of ethylene carbonate and 70 ml (0.50 mol) of triethylamine was heated to reflux for 16 h. Distillation of the reaction mixture through a Vigreux column at normal pressure yielded the title compound as a colorless liquid.

Boiling point: 132° C.; MS (ESI): m/z=145 [M+H]$^+$.

b) N-Dimethylaminomethylene-2-(2-(2,2,2-trifluoroethoxy)ethoxy)-5-(2-(2,2,2-trifluoroacetamido)ethyl)benzenesulfonamide 16.5 ml (55.5 mmol) of methanesulfonyl chloride were slowly added dropwise to a solution of 8.0 g (55.5 mmol) of the compound of example 4a) and 7.8 ml (55.5 mmol) of triethylamine in 50 ml of absolute THF cooled to 0° C. After stirring at RT for 15 min, the deposited triethylammonium chloride was filtered off with suction and the filtrate was concentrated to dryness in vacuo. 6.7 g (30 mmol) of the 2-(2,2,2-trifluoroethoxy)ethyl methanesulfonate obtained were added to 5.7 g (15.5 mmol) of the compound of example 2b) and 10 g of potassium carbonate in 150 ml of absolute DMF and the resulting mixture was stirred at 110° C. for 3 h. The reaction solution was then poured onto 1 l of ice water. The solution was extracted repeatedly with EA and the combined EA extracts were washed with water, dried over sodium sulfate and concentrated. Drying in a high vacuum yielded 6.8 g of the title compound.

$R_f$ (SiO$_2$, EA)=0.32; MS (ESI): m/z=494 [M+H]$^+$.

c) 5-(2-Aminoethyl)-2-(2-(2,2,2-trifluoroethoxy)ethoxy)benzenesulfonamide

According to the process described in example 2d), starting from 2.5 g (5.1 mmol) of the compound of example 4b), 1.3 g of the title compound were obtained using hydrochloric acid.

$R_f$ (SiO$_2$, EA)=0.06; MS (ESI): m/z=343 [M+H]$^+$.

d) 5-(2-(3-Quinolinecarboxamido)ethyl)-2-(2-(2,2,2-trifluoroethoxy)ethoxy)benzenesulfonamide According to the process described in example 1d), starting from 1.0 g (2.64 mmol) of the compound of example 4c) and 550 mg (3.17 mmol) of 3-quinolinecarboxylic acid, 1.18 g of the title compound were obtained as a white solid.

M.p.: 206–210 ° C.; $R_f$ (SiO$_2$, EA)=0.46; MS (ESI): m/z=498 [M+H]$^+$.

e) 1-[5-(2-(3-Quinolinecarboxamido)ethyl)-2-(2-(2,2,2-trifluoroethoxy)ethoxy)phenyl-sulfonyl]-3-methyl-thiourea According to the process described in example 1e), starting from 120 mg (0.24 mmol) of the compound of example 4d) and 295 μl (0.26 mmol) of a 1M solution of methyl isothiocyanate in absolute DMF, 85 mg of the title compound were obtained as a white solid after drying in a high vacuum.

M.p.: 115–120° C.; $R_f$ (SiO$_2$, EA)=0.52; MS (ESI): m/z= 571 [M+H]$^+$.

EXAMPLE 5

1-[5-(2-(3-Quinolinecarboxamido)ethyl)-242-(2,2,2-trifluoroethoxy)ethoxy)phenyl-sulfonyl]-3-methyl-thiourea Sodium Salt

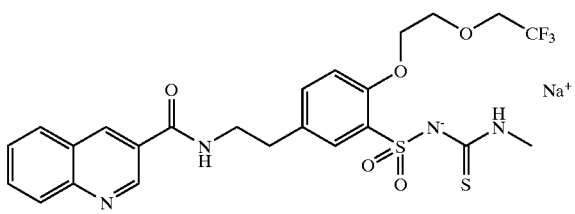

11 mg (0.28 mmol) of sodium hydroxide were dissolved in 5 ml of absolute ethanol. 150 mg (0.26 mmol) of the compound of example 4e) were then added and the resulting solution was stirred at RT for 5 h. The precipitate crystallizing from the solution was filtered off with suction and dried in a high vacuum. 135 mg of the title compound resulted as a white solid.

M.p.: 125° C.; MS (FAB): m/z=571 [M−Na+H]$^+$, 593 [M+H]$^+$.

EXAMPLE 6

1-[5(2-(3Quinolinecarboxamido)ethyl)-2-(2(2,2,2-trifluoroethoxy)ethoxy)phenyl-sulfonyl]-3-methyl-urea

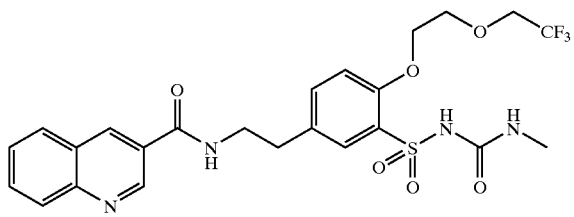

According to the process described in example 3), starting from 40 mg (0.07 mmol) of the compound of example 4e), 24 mg of the title compound were obtained as a pale yellow solid using hydrogen peroxide.

M.p.: 128° C.; $R_f$ (SiO$_2$, EA)=0.47; MS (ESI): m/z=555 [M+H]$^+$.

EXAMPLE 7

1-[5-(2-(3-Quinolinecarboxamido)ethyl)-2-ethoxyphenylsulfonyl]-3-methyl-thiourea

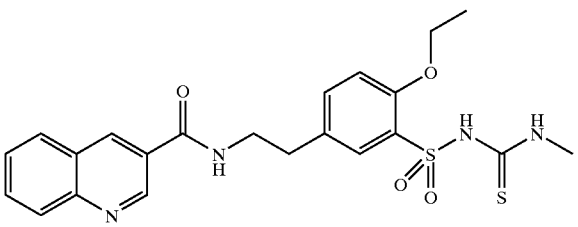

a) N-Dimethylaminomethylene-2-ethoxy-5-(2-(2,2,2-trifluoroacetamido)ethyl)-benzenesulfonamide A mixture of 2.0 g (5.44 mmol) of the compound of example 2b) and 1.88 g (13.61 mmol) of potassium carbonate in 10 ml of absolute DMF was treated with 1.42 ml (19.05 mmol) of ethyl bromide and stirred at 70° C. for 2 h. The reaction solution was then treated with about 10 ml of EA. The solution was washed with water and saturated sodium chloride solution, and the organic phase was dried over sodium sulfate and concentrated to dryness. The resulting residue was triturated with a little EA and the precipitate which remained was filtered off with suction. Drying in a high vacuum yielded 915 mg of the title compound as a white solid.

M.p.: 148–150° C.; $R_f$ (SiO$_2$, EA)=0.57; MS (FAB): m/z=396 [M+H]$^+$.

b) 5-(2-Aminoethyl)-2-ethoxybenzenesulfonamide

According to the process described in example 1c), starting from 910 mg (2.31 mmol) of the compound of example 7a), 490 mg of the title compound were obtained as a white solid using hydrochloric acid.

M.p.: 241–243° C.; $R_f$ (SiO$_2$, EA)=0.03; MS (ESI): m/z=281 [M+H]$^+$.

c) 5-(2-(3-Quinolinecarboxamido)ethyl)-2-ethoxybenzenesulfonamide

According to the process described in example 1d), starting from 485 mg (1.73 mmol) of the compound of example 7b), 500 mg of the title compound were obtained as an amorphous white solid.

M.p.: 222–231° C.; $R_f$ (SiO$_2$, EA)=0.45; MS (ESI): m/z=400 [M+H]$^+$.

d) 1-[5-(2-(3-Quinolinecarboxamido)ethyl)-2-ethoxyphenylsulfonyl]-3-methyl-thiourea According to the process described in example 1e), starting from 495 mg (1.24 mmol) of the compound of example 7c), 222 mg of the title compound were obtained as a white solid using methyl isothiocyanate.

M.p.: 189–193° C.; $R_f$ (SiO$_2$, EA)=0.42; MS (ESI): m/z=473 [M+H]$^+$.

EXAMPLE 8

1-[5-(2-(3-Quinolinecarboxamido)ethyl)-2-propyloxyphenylsulfonyl]-3-methyl-thiourea

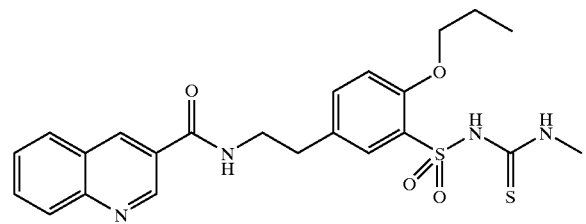

a) N-Dimethylaminomethylene-2-propyloxy-5-(2-(2,2,2-trifluoroacetamido)ethyl)-benzenesulfonamide According to the process described in example 7a), starting from 1.3 g (3.54 mmol) of the compound of example 2b), with n-propyl bromide, 771 mg of the title compound were obtained as a white solid after chromatographic purification on silica gel using EA/n-heptane (8:1).

M.p.: 142° C.; $R_f$ (SiO$_2$, EA)=0.58; MS (ESI): m/z=410 [M+H]$^+$.

b) 5-(2-Aminoethyl)-2-propyloxybenzenesulfonamide

According to the process described in example 1c), starting from 768 mg (1.87 mmol) of the compound of example 8a), 418 mg of the title compound were obtained as a white solid using hydrochloric acid.

M.p.: 224–230° C.; $R_f$ (SiO$_2$, EA)=0.03; MS (DCl): m/z=295 [M+H]$^+$.

c) 5-(2-(3-Quinolinecarboxamido)ethyl)-2-propyloxybenzenesulfonamide

According to the process described in example 1d), starting from 414 mg (1.40 mmol) of the compound of example 8b), 302 mg of the title compound were obtained as an amorphous white solid using 3-quinolinecarboxylic acid.

$R_f$ (SiO$_2$, EA)=0.24; MS (ESI): m/z=414 [M+H]$^+$.

d) 1-[5-(2-(3-Quinolinecarboxamido)ethyl)-2-Propyloxyphenylsulfonyl]-3-methyl-thiourea According to the process described in example 1e), starting from 296 mg (0.72 mmol) of the compound of example 8c), 321 mg of the title compound were obtained as a white solid using methyl isothiocyanate.

M.p.: 108–110° C.; $R_f$ (SiO$_2$, EA)=0.47; MS (ESI): m/z=487 [M+H]$^+$.

EXAMPLE 9

1-[5-(2-(3-Quinolinecarboxamido ethyl)-2-propyloxyphenylsulfonyl]-3-methyl-urea

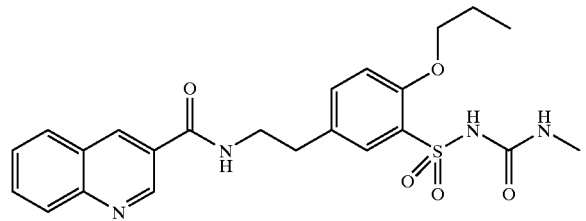

According to the process described in example 3), starting from 70 mg (0.14 mmol) of the compound of example 8d), 37 mg of the title compound were obtained as a pale yellow solid using hydrogen peroxide.

M.p.: 120° C.; Rf (SiO2, EA)=0.38; MS (FAB): m/z=471 [M+H]$^+$.

EXAMPLE 10

1-[5-(2-(3-Quinolinecarboxamido)ethyl)-2-(2-ethoxyethoxy)phenylsulfonyl]-3-methyl-thiourea

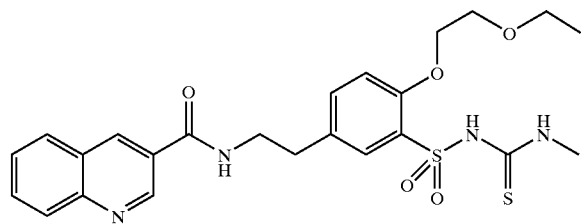

a) N-Dimethylaminomethylene-(2-(2-ethoxyethoxy)-5-(2-(2,2,2-trifluoroacetamido)-ethyl)benzenesulfonamide A mixture of 2.0 g (5.44 mmol) of the compound of example 2b) and 1.88 g (6.80 mmol) of potassium carbonate in 10 ml of absolute DMF was treated with 2.14 ml (13.61 mmol) of 2-bromoethyl ethyl ether and stirred at 70° C. for 1.5 h. The reaction mixture was then treated with about 10 ml of EA. The mixture was washed with water and saturated sodium chloride solution, and the organic phase was dried over sodium sulfate and concentrated to dryness. The residual colorless oil was purified by chromatography on silica gel using EA/n-heptane (8:1). Concentration of the product-containing fractions and drying in a high vacuum yielded 1.35 g of the title compound as a pale yellow solid.

M.p.: 88–91° C.; $R_f$ (SiO$_2$, EA)=0.40; MS (ESI): m/z=440 [M+H]$^+$.

b) 5-(2-Aminoethyl)-2-(2-ethoxyethoxy)benzenesulfonamide

According to the process described in example 1c), starting from 1.33 g (3.03 mmol) of the compound of example 10a), 700 mg of the title compound were obtained as a white solid using hydrochloric acid.

M.p.: 203–205° C.; $R_f$ (SiO$_2$, EA)=0.04; MS (ESI): m/z=289 [M+H]$^+$.

c) 5-(2-(3-Quinolinecarboxamido)ethyl)-2-(2-ethoxyethoxy)benzenesulfonamide

According to the process described in example 1d), starting from 695 mg (2.15 mmol) of the compound of example 10b), 754 mg of the title compound were obtained as a white solid using 3-quinolinecarboxylic acid.

M.p.: 220–226° C.; $R_f$ (SiO$_2$, EA)=0.33; MS (ESI): m/z=444 [M+H]$^+$.

d) 1-[5-(2-(3-Quinolinecarboxamido)ethyl)-2-(2-ethoxyethoxy)phenylsulfonyl]-3-methyl-thiourea According to the process described in example 1e), starting from 750 mg (1.69 mmol) of the compound of example 10c), 219 mg of the title compound were obtained as a pale yellow solid using methyl isothiocyanate.

M.p.: 50–52° C.; $R_f$(SiO$_2$, EA)=0.47; MS (ESI): m/z=517 [M+H]$^+$.

EXAMPLE 11

1-[5-(2-(3-Quinolinecarboxamido)ethyl)-2-(2-phenoxyethoxy)phenylsulfonyl]-3-methyl-thiourea

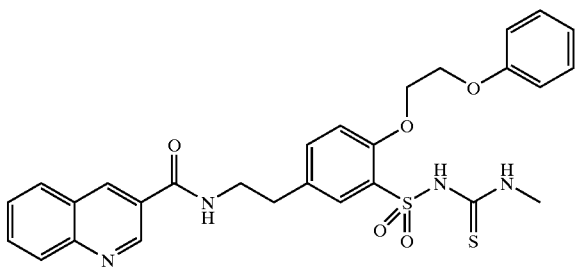

a) N-Dimethylaminomethylene-(2-(2-phenoxyethoxy)-5-(2-(2,2,2-trifluoroacetamido)-ethyl)benzenesulfonamide According to the process described in example 2c), starting from 1.0 g (2.72 mmol) of the compound of example 2b) and 1.91 g (9.53 mmol) of 2-phenoxyethyl bromide, 886 mg of the title compound were obtained as a white solid.

M.p.: 89–91° C.; $R_f$(SiO$_2$, EA)=0.57; MS (ESI): m/z=488 [M+H]$^+$.

b) 5-(2-Aminoethyl)-2-(2-phenoxyethoxy)benzenesulfonamide

According to the process described in example 1c), starting from 880 mg (1.81 mmol) of the compound of example 11a), 656 mg of the title compound were obtained as a white solid using hydrochloric acid.

M.p.: 215° C.; $R_f$ (SiO$_2$, EA)=0.02; MS (DCI): m/z=337 [M+H]$^+$.

c) 5-(2-(3-Quinolinecarboxamido)ethyl)-2-(2-phenoxyethoxy)benzenesulfonamide

According to the process described in example 1d), starting from 252 mg (0.68 mmol) of the compound of example 11b), 222 mg of the title compound were obtained as a white solid using 3-quinolinecarboxylic acid.

M.p.: 205–209° C.; $R_f$(SiO$_2$, EA)=0.62; MS (ESI): .m/z=492 [M+H]$^+$.

d) 1-[5-(2-(3-Quinolinecarboxamido)ethyl)-2-(2-phenoxyethoxyphenylsulfonyl]-3-methyl-thiourea According to the process described in example 1e), starting from 108 mg (0.22 mmol) of the compound of example 11c), 121 mg of the title compound were obtained as a slightly yellow solid using methyl isothiocyanate.

M.p.: 110° C.; $R_f$ (SiO$_2$, EA)=0.48; MS (ESI): m/z=565 [M+H]$^+$.

EXAMPLE 12

1-[5-(2-(3-Quinolinecarboxamido)ethyl)-2-(2-phenylethoxy)phenylsulfonyl]-3-methyl-thiourea

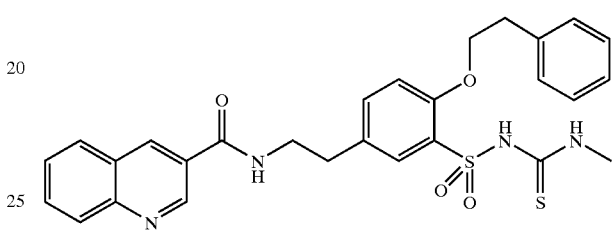

a) N-Dimethylaminomethylene-2-(2-phenylethoxy)-5-(2-(2,2,2-trifluoroacetamido)-ethyl)benzenesulfonamide According to the process described in example 9a), starting from 1.5 g (4.01 mmol) of the compound of example 2b), 1.21 g of the title compound were obtained as a white solid using 2-phenylethyl bromide.

M.p.: 48° C.; $R_f$ (SiO$_2$, EA)=0.67; MS (ESI): m/z=472 [M+H]$^+$.

b) 5-(2-Aminoethyl)-2-(2-phenylethoxy)benzenesulfonamide

According to the process described in example 1c), starting from 1.2 g (2.54 mmol) of the compound of example 12a), 880 mg of the title compound were obtained as a white solid using hydrochloric acid.

M.p.: 207–212° C.; $R_f$ (SiO$_2$, EA)=0.73; MS (ESI): m/z=321 [M+H]$^+$.

c) 5-(2-(3-Quinolinecarboxamido)ethyl)-2-(2-phenylethoxy)benzenesulfonamide

According to the process described in example 1d), starting from 350 mg (0.98 mmol) of the compound of example 12b), 256 mg of the title compound were obtained as a white solid using 3-quinolinecarboxylic acid.

M.p.: 232–236° C.; $R_f$ (SiO$_2$, EA)=0.52; MS (ESI): m/z=476 [M+H]$^+$.

d) 1-[5-(2-(3-Quinolinecarboxamido)ethyl)-2-(2-phenylethoxy)phenylsulfonyl]-3-methyl-thiourea According to the process described in example 1e), starting from 125 mg (0.26 mmol) of the compound of example 12c), 140 mg of the title compound were obtained as a white solid using methyl isothiocyanate.

M.p.: 124° C.; $R_f$ (SiO$_2$, EA)=0.48; MS (FAB): m/z=549 [M+H]$^+$.

EXAMPLE 13

1-[5-(2-(3-Quinolinecarboxamido)ethyl)-2-(2,2,2-trifluoroethoxy)phenylsulfonyl]-3-methyl-thiourea

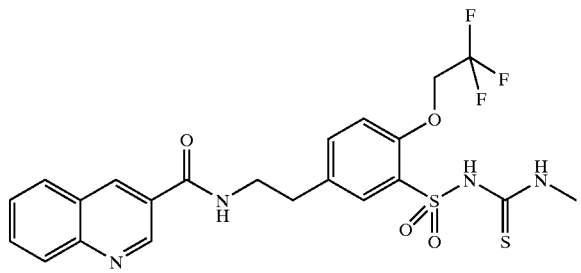

a) N-Dimethylaminomethylene-2-(2,2,2-trifluoroethoxy)-5-(2-(2,2,2-trifluoroacetamido)ethyl)benzenesulfonamide A solution of 1.44 ml (20.0 mmol) of 2,2,2-trifluoroethanol, 2.77 ml (20.0 mmol) of triethylamine and 1.6 ml (20.5 mmol) of methanesulfonyl chloride in 20 ml of absolute THF was stirred under an argon atmosphere for 15 min. The precipitated triethylammonium chloride was filtered off and the filtrate was evaporated. 2.7 g of 2,2,2-trifluoroethyl methanesulfonate remained as a colorless liquid. 2.68 g (1 5.05 mmol) of this compound were dissolved in 80 ml of absolute DMF under an argon atmosphere, and 4.57 g (33.10 mmol) of potassium carbonate and 2.21 g (6.02 mmol) of the compound of example 2b) were added. The resulting reaction mixture was stirred at 110° C. for 3 h and then poured onto 500 ml of ice. The mixture was extracted repeatedly with EA, and the combined EA phases were dried over sodium sulfate and concentrated. Chromatographic purification of the residue on silica gel using EA yielded 1.20 g of the title compound as a white solid.

M.p.: 130° C.; $R_f$ (SiO$_2$, EA)=0.73; MS (ESI): m/z=450 [M+H]$^+$.

b) 5-(2-Aminoethyl)-2-(2,2,2-trifluoroethoxy)benzenesulfonamide

According to the process described in example 1c), starting from 1.14 g (2.53 mmol) of the compound of example 13a), 345 mg of the title compound were obtained as a white solid using hydrochloric acid.

M.p.: 241° C.; $R_f$ (SiO$_2$, EA)=0.02; MS (ESI): m/z=335 [M+H]$^+$.

c) 5-(2-(3-Quinolinecarboxamido)ethyl)-2-(2,2,2-trifluoroethoxy)benzenesulfonamide According to the process described in example 1d), starting from 340 mg (1.02 mmol) of the compound of example 13b), 66 mg of the title compound were obtained as a white solid using 3-quinolinecarboxylic acid.

M.p.: 196–202° C.; $R_f$ (SiO$_2$, EA)=0.40; MS (ESI): m/z= 453 [M+H]$^+$.

d) 1-[5-(2-(3-Quinolinecarboxamido)ethyl)-2-(2,2,2-trifluoroethoxy)phenylsulfonyl]-3-methyl-thiourea According to the process described in example 1e), starting from 55 mg (0.12 mmol) of the compound of example 13c), 52 mg of the title compound were obtained as a pale yellow solid using methyl isothiocyanate.

M.p.: 75° C.; $R_f$ (SiO$_2$, EA)=0.28; MS (ESI): m/z=527 [M+H]$^+$.

EXAMPLE 14

1-[5-(2-(3-Quinolinecarboxamido)ethyl)-2-(2-furyl)phenylsulfonyl]-3-methyl-thiourea

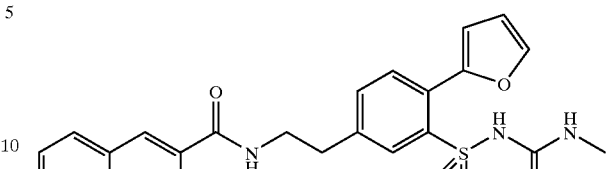

a) 2,2,2-Trifluoro-N-(2-(4-nitrophenyl)ethyl)acetamide

According to the process described in example 1a), starting from 29.8 g (0.15 mol) of 2-(4-nitrophenyl)ethylamine hydrochloride, 34.7 g of the title compound were obtained as a beige solid using trifluoroacetic anhydride.

M.p.: 96–97° C.; $R_f$ (SiO$_2$, EA/heptane 1:1)=0.52; MS (ESI): m/z=263 [M+H]$^+$.

b) 2,2,2-Trifluoro-N-(2-(4-aminophenyl)ethyl)acetamide

A solution of 34.6 g (0.13 mol) of the compound of example 14a) and 197 g (0.87 mol) of SnCl$_2$×2 H$_2$O in 1 l of EA was stirred at 80° C. for 3.5 h. The reaction solution was then treated with 2 l of 10% strength sodium hydrogencarbonate solution, the precipitate was filtered off and the organic phase was separated. The organic phase was dried over sodium sulfate and concentrated to dryness in vacuo. 26.9 g of the title compound resulted as a pale brown solid.

M.p.: 81–85° C.; $R_f$ (SiO$_2$, EA/heptane 1:1)=0.35; MS (ESI): m/z=233 [M+H]$^+$.

c) 2,2,2-Trifluoro-N-(2-(4-iodophenyl)ethyl)acetamide

A solution of 8.3 g (0.12 mol) of sodium nitrite in 28 ml of water was added dropwise to a suspension of 26.8 g (0.11 mol) of the compound of example 14b) in 125 ml of dilute hydrochloric acid cooled to 0° C. After stirring at this temperature for 15 min, a solution of 19.9 g (0.12 mol) of potassium iodide in 28 ml of water was added dropwise and the resulting reaction solution was stirred at RT for 3 h. The solution was extracted with DCM, and the organic phase was separated off, washed with 10% strength sodium hydrogensulfite solution and water and dried over sodium sulfate. After concentration and chromatographic purification of the residue on silica gel using DCM/EA(80:1), 17.1 g of the title compound were obtained as a pale yellow solid.

M.p.: 136–138° C.; $R_f$ (SiO$_2$, EA/heptane 1:1)=0.67; MS (DCI): m/z=344 [M+H]$^+$.

d) 2-Iodo-5-(2-(2,2,2-trifluoroacetamido)ethyl)benzenesulfonamide 10 g (29.1 mmol) of the compound of example 14c) were added in portions to 95 ml of chlorosulfonic acid cooled to 0° C. After stirring at RT for 3.5 h, the reaction solution was added dropwise to 400 ml of ice and the deposited precipitate was filtered off with suction. This precipitate was dissolved in 200 ml of acetone, and 56 ml of concentrated ammonia solution were added dropwise to this solution with ice-cooling. After stirring at RT for 45 min, the deposited precipitate was filtered off with suction and the acetone was evaporated in a rotary evaporator. The solution that remained was extracted with EA, and the EA phase was separated off, washed with saturated sodium chloride solution and dried over sodium sulfate. After concentration and chromatographic purification of the residue on silica gel using EA/heptane (1:2), 4.5 g of the title compound were obtained.

M.p.: from 115° C. (softening); $R_f$ (SiO$_2$, EA/heptane 1:1)=0.32; MS (ESI): m/z=423 [M+H]$^+$.

e) N-Dimethylaminomethylene-2-iodo-5-(2-(2,2,2-trifluoroacetamido)ethyl)benzenesulfonamide A solution of 2.9 g (6.87 mmol) of the compound of example 14d) and 1.26 ml (8.26 mmol) of N,N-dimethylformamide dimethyl acetal in 16 ml of absolute DMF was stirred at RT for 1 h. The mixture was concentrated to dryness in vacuo and the residue was dissolved in 5 ml of DMF. 70 ml of a 5% strength sodium hydrogensulfate solution was added dropwise to this solution at 0° C., and the deposited precipitate was filtered off with suction and washed with water. Drying in a high vacuum yielded 3.2 g of the title compound as a slightly yellow solid.

M.p.: 155–156° C.; $R_f$ (SiO$_2$, EA/heptane 1:1)=0.10; MS (ESI): m/z=478 [M+H]$^+$.

f) N-Dimethylaminomethylene-2-(2-furyl)-5-(2-(2,2,2-trifluoroacetamido)ethyl)-benzenesulfonamide 26.6 mg (0.03 mmol) of bis(triphenylphosphine) palladium(II) chloride and 2.9 ml (9.28 mmol) of 2-(tri-n-butylstannyl)furan were added under an argon atmosphere to a solution of 3.1 g (6.70 mmol) of the compound of example 14e) in 30 ml of DMF. The resulting reaction solution was heated to reflux for 8 h. The solution was then diluted with EA, and washed with water and dried over sodium sulfate. Chromatographic purification of the residue which remained after stripping off the solvent, on silica gel using EA/n-heptane (1:1) afforded 2.6 g of the title compound as a pale yellow solid.

M.p.: 150° C.; $R_f$ (SiO$_2$, EA/heptane 1:1)=0.06; MS (ESI): m/z=418 [M+H]$^+$.

g) 5-(2-Aminoethyl )-2-(2-furyl)benzenesulfonamide

A solution of 2.6 g (6.23 mmol) of the compound of example 14f) and 9 ml of 2N sodium hydroxide solution in 46 ml of ethanol was stirred at 80° C. for 2 h. After cooling to RT, the pH of the solution was adjusted to 7 by addition of concentrated acetic acid, and the solution was concentrated to dryness. Drying of the residue in a high vacuum yielded 1.6 g of the title compound as a colorless oil.

$R_f$ (SiO$_2$, EA)=0.10; MS (ESI): m/z=267 [M+H]$^+$.

h) 5-(2-(3-Quinolinecarboxamido)ethyl)-2-(2-furyl)benzenesulfonamide

According to the process described in example 1d), starting from 1.5 g (1.68 mmol) of the compound of example 14 g), 536 mg of the title compound were obtained as a white solid using 3-quinolinecarboxylic acid.

M.p.: 196° C.; $R_f$ (SiO$_2$, EA/n-heptane 4:1)=0.12; MS (ESI): m/z =422 [M+H]$^+$.

i) 1-[5-(2-(3-Quinolinecarboxamido)ethyl)-2-(2-furyl)phenylsulfonyl]-3-methyl-thiourea According to the process described in example 1e), starting from 260 mg (0.62 mmol) of the compound of example 14h), 210 mg of the title compound were obtained as an amorphous solid using methyl isothiocyanate.

$R_f$ (SiO$_2$, EA/n-heptane 4:1)=0.28; MS (ESI): m/z =495 [M+H]$^+$.

EXAMPLE 15

1-[5-(2-(3-Methylbut-2-eneamido)ethyl)-2-methoxyphenylsulfonyl]-3-methyl-thiourea

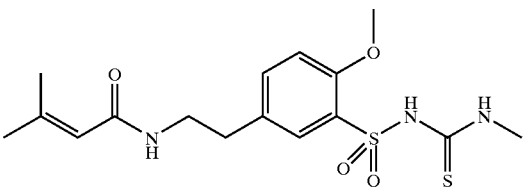

a) 5-(2-(3-Methylbut-2-eneamido)ethyl)-2-methoxybenzenesulfonamide

According to the process described in example 1d), starting from 465 mg (2.02 mmol) of the compound of example 1c), 199 mg of the title compound were obtained as a white solid using 3,3-dimethylacrylic acid.

M.p.: 156–160° C.; $R_f$ (SiO$_2$, EA/n-heptane 4:1)=0.21; MS (ESI): m/z=313 [M+H]$^+$.

b) 1-[5-(2-(3-Methylbut-2-eneamido)ethyl)-2-methoxyphenylsulfonyl]-3-methyl-thiourea According to the process described in example 1e), starting from 90 mg (0.30 mmol) of the compound of example 15a), 66 mg of the title compound were obtained as a white solid using methyl isothiocyanate.

M.p.: 153–154° C.; $R_f$ (SiO$_2$, EA/n-heptane 8:1)=0.42; MS (ESI): m/z=386 [M+H]$^+$.

EXAMPLE 16

1-[5-(2-(3-Methylbut-2-eneamido)ethyl)-2-methoxyphenylsulfonyl]-3-methyl-urea

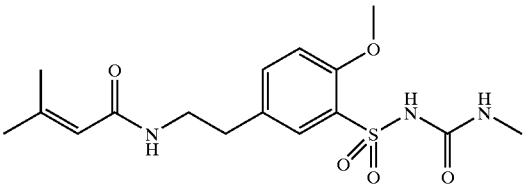

According to the process described in example 3), starting from 45 mg (0.12 mmol) of the compound of example 15b), 17 mg of the title compound were obtained as a white solid using hydrogen peroxide.

M.p.: 199–203° C.; $R_f$ (SiO$_2$, EA/n-heptane 8:1)=0.09; MS (ESI): m/z=370 [M+H]$^+$.

EXAMPLE 17

1-[5-(2-(3-Methylbut-2-eneamido)ethyl)-2-(2-methoxyethoxy)phenylsulfonyl]-3-methyl-thiourea

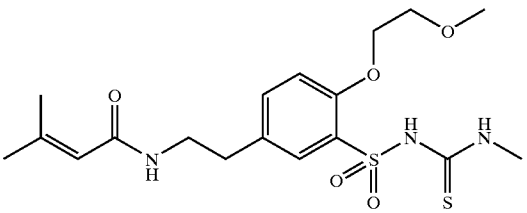

a) 5-(2-(3-Methylbut-2-eneamido)ethyl)-2-(2-methoxyethoxy)benzenesulfonamide

According to the process described in example 1d), starting from 500 mg (1.61 mmol) of the compound of example 2c), 190 mg of the title compound were obtained as a white solid using 3,3-dimethylacrylic acid.

M.p.: 120–127° C.; $R_f$ (SiO$_2$, EA/n-heptane 4:1)=0.15; MS (ESI): m/z=357 [M+H]$^+$.

b) 1-[5-(2-(3-Methylbut-2-eneamido)ethyl)-2-(2-methoxyethoxy)phenylsulfonyl]-3-methyl-thiourea According to the process described in example 1e), starting from 185 mg (0.53 mmol) of the compound of example 17a), 68 mg of the title compound were obtained as a white amorphous solid using methyl isothiocyanate.

$R_f$ (SiO$_2$, EA/n-heptane 4:1)=0.37; MS (ESI): m/z=430 [M+H]$^+$.

EXAMPLE 18

1-[5-(2-(1-Cyclohex-1-enecarboxamido)ethyl)-2-methoxyphenylsulfonyl]-3-methyl-thiourea

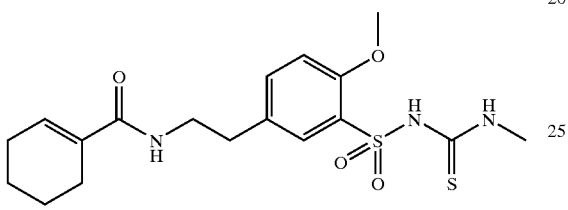

a) 5-(2-(1-Cyclohex-1-enecarboxamido)ethyl)-2-methoxybenzenesulfonamide

According to the process described in example 1d), starting from 465 mg (2.02 mmol) of the compound of example 1c), 598 mg of the title compound were obtained as a white solid using 1-cyclohex-1-enecarboxylic acid.

M.p.: 155–157° C.; $R_f$ (SiO$_2$, EA/n-heptane 4:1)=0.21; MS (ESI): m/z=339 [M+H]$^+$.

b) 1-[5-(2-(1-Cyclohex-1-enecarboxamido)ethyl)-2-methoxyphenylsulfonyl]-3-methyl-thiourea According to the process described in example 1e), starting from 197 mg (0.58 mmol) of the compound of example 18a), 204 mg of the title compound were obtained as a white solid using methyl isothiocyanate.

M.p.: 179–182° C.; $R_f$ (SiO$_2$, EA/n-heptane 8:1)=0.42; MS (ESI): m/z=412 [M+H]$^+$.

EXAMPLE 19

1-[5-(2-(1-Cyclohex-1-enecarboxamido)ethyl)-2-methoxyphenylsulfonyl]-3-methyl-urea

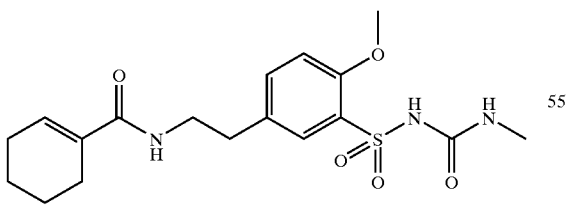

According to the process described in example 3), starting from 70 mg (0.17 mmol) of the compound of example 18b), 57 mg of the title compound were obtained as a white solid using hydrogen peroxide.

M.p.: 175° C.; $R_f$ (SiO$_2$, EA/n-heptane 8:1)=0.15; MS (ESI): m/z=396 [M+H]$^+$.

EXAMPLE 20

1-[5-(2-(1-Cyclohex-1-enecarboxamido)ethyl)-2-methoxyphenylsulfonyl]-3-isopropyl-thiourea

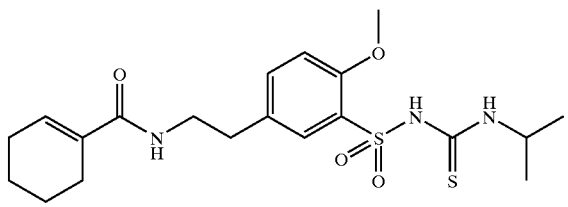

According to the process described in example 1e), starting from 197 mg (0.58 mmol) of the compound of example 18a), 213 mg of the title compound were obtained as a white solid using isopropyl isothiocyanate.

M.p.: 80–85° C.; $R_f$ (SiO$_2$, EA/n-heptane 8:1)=0.50; MS (ESI): m/z=440 [M+H]$^+$.

EXAMPLE 21

1-[5-(2-(1-Cyclohex-1-enecarboxamido)ethyl)-2-methoxyphenylsulfonyl]-3-cyclohexyl-thiourea

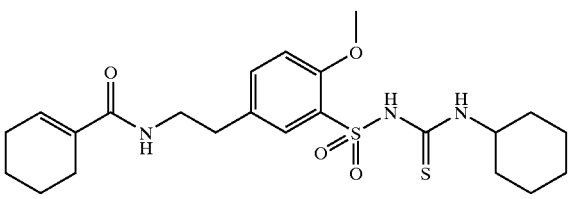

According to the process described in example 1e), starting from 197 mg (0.58 mmol) of the compound of example 18a), 272 mg of the title compound were obtained as a white solid using cyclohexyl isothiocyanate.

M.p.: 171–173° C.; Rf (SiO2, EA/n-heptane 8:1)=0.53; MS (ESI): m/z=480 [M+H]$^+$.

EXAMPLE 22

1-[5-(2-(1-Cyclohex-1-enecarboxamido)ethyl)-2-(2-methoxyethoxy)phenylsulfonyl]-3-methyl-thiourea

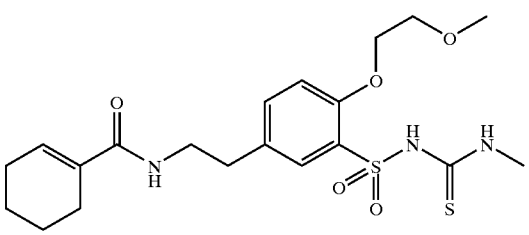

a) 5-(2-(1-Cyclohex-1-enecarboxamido)ethyl)-2-(2-methoxyethoxy)benzenesulfonamide According to the process described in example 1d), starting from 500 mg (1.61 mmol) of the compound of example 2c), 280 mg of the title compound were obtained as a pale yellow solid using 1-cyclohex-1-enecarboxylic acid.

M.p.: 165–172° C.; $R_f$ (SiO$_2$, EA/n-heptane 4:1)=0.11; MS (ESI): m/z=383 [M+H]$^+$.

b) 1-[5-(2-(1-Cyclohex-1-enecarboxamido)ethyl)-2-(2-methoxyethoxy)phenylsulfonyl]-3-methyl-thiourea According to the process described in example 1e), starting from 135 mg (0.35 mmol) of the compound of example 22a), 106 mg of the title compound were obtained as a beige solid using methyl isothiocyanate.

M.p.: 150–155° C.; $R_f$ (SiO$_2$, EA/n-heptane 8:1) 0.22; MS (ESI): m/z=456 [M+H]$^+$.

PHARMACOLOGICAL INVESTIGATIONS

EXAMPLE 23

Action Potential Duration on the Papillary Muscle of the Guinea Pig

ATP deficiency states observed during ischemia in the cardiac muscle cell, lead to a shortening of the action potential duration (ATP=adenosine triphosphate). They are regarded as one of the causes of so-called reentry arrhythmias, which can cause sudden cardiac death. The opening of ATP-sensitive potassium channels by the lowering of the ATP level is regarded as the cause of this. For the measurement of the action potential on the papillary muscle of the guinea pig a standard microelectrode technique was employed.

Guinea pigs of both sexes were killed by a blow to the head, the hearts were removed, and the papillary muscles were separated out and suspended in an organ bath. The organ bath was rinsed with Ringer's solution (136 mmol/l of NaCl, 3.3 mmol/l of KCl, 2.5 mmol/l of CaCl$_2$, 1.2 mmol/l of KH$_2$PO$_4$, 1.1 mmol/l of MgSO$_4$, 5.0 mmol/l of glucose, 10.0 mmol/l of 1-(2-hydroxyethyl)piperazine4-(2-ethanesulfonic acid) (HEPES), pH adjusted to 7.4 with NaOH) and aerated with 100% oxygen at a temperature of 37° C. The muscle was stimulated with square-wave pulses of 1 V and 1 ms duration and a frequency of 1 Hz by means of an electrode. The action potential was derived and recorded by means of a glass microelectrode inserted intracellularly, which was filled with 3 mol/l of KCl solution. The compound to be tested was added to the Ringer's solution in a concentration of 2 μmol/l. The action potential was amplified using an amplifier from Hugo Sachs (March-Hugstetten, Germany) and stored and analyzed by means of a computer. The duration of the action potential was determined at a degree of repolarization of 90% (APD$_{90}$). After an equilibration time of 30 min, the action potential shortening was produced by rinsing the papillary muscle with a hypoxic NaCl solution. The glucose was removed here, the HEPES buffer replaced by PIPES buffer (piperazine-1,4-bis(2-ethanesulfonic acid)), the pH was adjusted to 6.5 and the aeration was carried out using 100% nitrogen. After a time of 60 min, this led to a marked shortening of the APD$_{90}$. After this time, the test compound was added and the relengthening of the action potential recorded after a further 60 min. The compound-caused relengthening of the APD$_{90}$ was calculated as a percentage, in relation to the shortening caused by hypoxia. The test compounds were added to the bath solution as stock solution in propanediol.

The following relengthenings of the APD$_{90}$ values were observed.

| Compound | Concentration | Relengthening of the APD$_{90}$ shortened by hypoxia |
| --- | --- | --- |
| Example 2 | 2 μM | 42% |
| Example 4 | 2 μM | 69% |
| Example 8 | 2 μM | 35% |
| Example 17 | 2 μM | 34% |

The observed values confirm the normalizing action of the compounds according to the invention on a hypoxically shortened action potential duration.

EXAMPLE 24

Chloroform-induced Ventricular Fibrillation in the Mouse (Action in the Case of Vagal Dysfunction)

Hypoactivity of the vagal nervous system leads to hyperactivity of the sympathetic nervous system. Damages to health that result from an inequilibrium of the autonomic nervous system when the dysfunction affects the heart include the weakening of the myocardial contractile force and fatal cardiac arrhythmias such as ventricular fibrillation. The action of the test compounds was investigated in the model of chloroform-induced ventricular fibrillation in the mouse (see J. W. Lawson, Antiarrhythmic activity of some isoquinoline derivatives determined by a rapid screening procedure in the mouse; J. Pharmacol. Exp. Ther. 160 (1968) 22).

The test compound was dissolved in a mixture of dimethyl sulfoxide (DMSO) and 10 percent sodium hydrogencarbonate solution and administered intraperitoneally (i.p.). The dose was 3 mg/kg. 30 min later, the mouse was anesthetized with chloroform in a beaker. As soon as respiratory arrest had occurred under deep anesthesia (toxic stage of anesthesia), the thorax of the animal was opened using a pair of scissors and the heartbeat was visually inspected. It can be determined here at a glance whether the heart is beating, fibrillating, or has stopped. The respiratory arrest induced by chloroform leads, via an absolute anoxia (oxygen deficiency) in combination with a direct stimulating action of chloroform on the sympathetic nervous system to a strong stimulation of the sympathetic nervous system, which in turn, and in combination with the energy deficiency caused by oxygen deficiency, leads in the heart to the fatal arrhythmia, ventricular fibrillation. This toxic chloroform anesthesia led to ventricular fibrillation in 100% of the untreated mice (control). The percentage proportion of the mice with ventricular fibrillation in the individual test groups (consisting of n animals) is indicated as the fibrillation ratio.

The following fibrillation ratios were observed.

| Compound | Fibrillation ratio (in %) |
| --- | --- |
| Untreated control (n = 300) | 100% |
| Example 20 (n = 10) | 70% |
| Example 21 (n = 10) | 70% |

The reduction of the percentage proportion of mice having ventricular fibrillation in comparison with the control (with a 100% fibrillation ratio) confirms that the compounds of the invention significantly prevent the occurrence of ventricular fibrillation.

EXAMPLE 25

Action on hSUR1/hKir6.2-transfected CHO Cells (Hypoglycemic Action)

The mechanism of action of hypoglycemic sulfonylureas such as, for example, glibenclamide has been roughly elucidated. The target organ of these compounds is the D cell of the pancreas where they block ATP-sensitive potassium channels and produce a release of the hypoglycemic hormone insulin by influencing the electrical potential of the cell membrane.

In molecular biology terms, pancreatic ATP-sensitive potassium channels are composed of the sulfonylurea receptor SUR1 and the inwardly rectifying potassium channel Kir6.2 (Inagaki et al., Science 270 (1995) 1166; Inagaki et al., Neuron 16 (1996) 1011). A hypoglycemic compound such as, for example, glibenclamide brings about, by binding to the sulfonylurea receptor, a depolarization of the cell membrane, which leads to an increased influx of calcium ions, and as a consequence thereof, to a release of insulin. The extent of this depolarization of the cell membrane, which is caused by the compounds according to the invention, was investigated on CHO cells that were transfected with the cloned components of human pancreatic ATP-sensitive potassium channels, hSUR1, and hKir6.2, and activated by pretreatment with diaxozide, an opener of ATP-sensitive potassium channels. The potency of a compound with respect to the membrane potential of these transfected and activated CHO cells is a measure of the hypoglycemic potential of this compound.

The CHO cells that showed a stable expression of human SUR1 and Kir6.2 were inoculated into 96-well microtiter plates on the day before measurement. On the day of measurement, the microtiter plates were washed three times with PBS (physiological buffer solution). In the last washing step, 90 µl remained in each well. The cells were then loaded with the fluorescent dye $DIBAC_4$ (Molecular Probes, Portland, Oreg., USA) by addition of 90 µl of a 10-micromolar solution of $DIBAC_4$ in PBS and of 90 µl of a 400 micromolar solution of diaxozide in PBS to each well. After an incubation time of 30 min at 37° C., the microtiter plates were then transferred to a fluorescent microtiter plate reader (FLIPR; Molecular Devices, Sunnyvale, Calif., USA). The cells were stimulated by means of an argon laser (Innova 90; Coherent, Santa Clara, Calif., USA) at a wavelength of 488 nm and the fluorescence emission was measured by means of a CCD camera. The measurement of the membrane potential began after 4 min by addition of 20 µl of a solution of the test compound or of the control solution to each well, the resulting fluorescence emission being measured every 20 seconds for a period of 20 min. The data shown are mean values of at least 4 experiments.

The following results were obtained.

| Compound | Concentration | Blockade hSUR1/hKir6.2 |
|---|---|---|
| Glibenclamide (hypoglycemic comparison substance) | 0.01 µM | 92.7% |
| Example 2 | 10 µM | 6.1% |
| Example 3 | 10 µM | 0% |
| Example 4 | 10 µM | 69.8% |
| Example 11 | 10 µM | 67.5% |
| Example 20 | 10 µM | 38.3% |

The obtained results confirm that the compounds according to the invention have no or an only very slight hypoglycemic action.

We claim:
1. A compound of the formula (I),

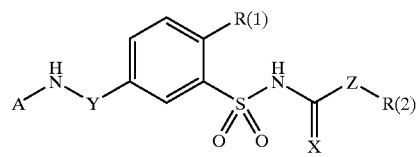

wherein
R(1) is
a) $(C_1–C_4)$-alkyl; or
b) —O—$(C_1–C_4)$-alkyl, which is unsubstituted or is substituted by 1, 2, or 3 fluorine atoms; or
c) —O—$(C_1–C_4)$-alkyl which is substituted by a substituent chosen from nitro, (($C_1–C_4$)-alkyl)carbonylamino, ($C_1–C_4$)-alkylamino, di(($C_1–C_4$)-alkyl)amino, hydroxycarbonyl, (($C_1–C_4$)-alkoxy)carbonyl, piperidin-1-yl, morpholin-4-yl, tetrahydrofuranyl, tetrahydropyranyl, phenyl and phenoxy; wherein the phenyl group and the phenoxy group are unsubstituted or are substituted by one or two identical or different substituents chosen from halogen, ($C_1–C_4$)-alkyl, ($C_1–C_4$)-alkoxy, and trifluoromethyl; or
d) —O—$(C_1–C_4)$-alkyl-E(1)-$(C_1–C_4)$-alkyl-D(1), in which D(1) is hydrogen or —E(2)-$(C_1–C_4)$-alkyl-D(2), in which D(2) is hydrogen or —E(3)-$(C_1–C_4)$-alkyl, wherein E(1), E(2) and E(3), which are independent of one another and can be identical or different, are chosen from O, S, and NH; or
e) —O—$(C_1–C_4)$-alkyl-O—$(C_1–C_4)$-alkyl, which is substituted in the terminal alkoxy group by 1, 2, or 3 fluorine atoms; or
f) —O—$(C_2–C_4)$-alkenyl; or
g) —O-phenyl, which is unsubstituted or is substituted by one or two identical or different substituents chosen from halogen, ($C_1–C_4$)-alkyl, ($C_1–C_4$)-alkoxy, and trifluoromethyl; or
h) halogen; or
i) phenyl, which is unsubstituted or is substituted by one or two identical or different substituents chosen from halogen, ($C_1–C_4$)-alkyl, ($C_1–C_4$)-alkoxy, —S(O)$_m$—($C_1–C_4$)-alkyl, phenyl, amino, hydroxyl, nitro, trifluoromethyl, cyano, hydroxycarbonyl, carbamoyl, (($C_1–C_4$)-alkoxy)carbonyl, and formyl; or
j) $(C_2–C_5)$-alkenyl, which is unsubstituted or is substituted by a substituent chosen from phenyl, cyano, hydroxycarbonyl, and (($C_1–C_4$)-alkoxy)carbonyl; or
k) $(C_2–C_5)$-alkynyl, which is unsubstituted or is substituted by a substituent chosen from phenyl and ($C_1–C_4$)-alkoxy; or
l) 5-membered or 6-membered monocyclic heteroaryl having one or two identical or different ring heteroatoms chosen from oxygen, sulfur, and nitrogen; or
m) —S(O)$_m$-phenyl, which is unsubstituted or is substituted by one or two identical or different substituents chosen from halogen, ($C_1–C_4$)-alkyl, ($C_1–C_4$)-alkoxy and trifluoromethyl;
R(2) is hydrogen, $(C_1–C_6)$-alkyl, or $(C_3–C_7)$-cycloalkyl, but is not hydrogen if Z is oxygen;
the residues R(3), which are all independent of one another and can be identical or different, are hydrogen or $(C_1–C_3)$-alkyl;

A is chosen from:

[structures: 3-acylquinoline; 1-acylcyclohexene; 4-methylpent-3-en-2-one-like acyl], and wherein the free bond via which the residue A is bonded to the amino group in the formula (I) is represented by the symbol ——•;

X is oxygen or sulfur;

Y is —(CR(3)$_2$)$_n$—;

Z is NH or oxygen;

m is 0, 1 or 2;

n is 1, 2, 3 or 4;

or a stereoisomeric form of a compound of formula (I), or a mixture of at least two stereoisomeric forms of a compound of formula (I), or a physiologically tolerable salt of a compound of formula (I).

2. A compound as claimed in claim 1, wherein Z is NH.

3. A compound as claimed in claim 1, wherein R(1) is a) methyl, ethyl, or isopropyl; or b) methoxy, ethoxy, propoxy, trifluoromethoxy, 2-fluoroethoxy, or 2,2,2-trifluoroethoxy; or c) tetrahydrofuran-2-ylmethoxy, tetrahydropyran-2-ylmethoxy, 2-(morpholin-4-yl)ethoxy, 2-phenoxyethoxy, benzyloxy, or 2-phenylethoxy; or d) 2-methoxyethoxy or 2-ethoxyethoxy; or e) 2-(trifluoromethoxy)ethoxy or 2-(2,2,2-trifluoroethoxy)ethoxy; or f) allyloxy; or g) phenoxy, 4-fluorophenoxy, 4-methylphenoxy, 4-methoxyphenoxy or 4-trifluoromethylphenoxy; or h) bromine or iodine; or i) phenyl, 4-methylphenyl, 4-methoxyphenyl, 4-fluorophenyl or 4-trifluoromethylphenyl; or j) allyl; or k) ethynyl; or l) furyl, thienyl, or pyridyl; or m) —S-phenyl.

4. A compound as claimed in claim 1, wherein R(1) is methoxy, ethoxy, trifluoromethoxy, 2-methoxyethoxy, 2-ethoxyethoxy, 2-(trifluoromethoxy)ethoxy, 2-(2,2,2-trifluoroethoxy)ethoxy, tetrahydrofuran-2-ylmethoxy, tetrahydropyran-2-ylmethoxy, or benzyloxy.

5. A compound as claimed in claim 1, wherein R(2) is (C$_1$–C$_4$)-alkyl.

6. A compound as claimed in claim 1, wherein R(2) is methyl.

7. A process for the preparation of a compound as claimed in claim 1, comprising a) converting a benzenesulfonamide of the formula (III),

III into a benzenesulfonyl iso(thio)cyanate of the formula (VIII)

VIII b) reacting the compound of the formula (VIII) with an amine of the formula R(2)-NH$_2$ or an alcohol of the formula R(2)-OH to give a compound of the formula (I), and c) optionally reacting a compound of the formula (I) with a suitable reagent to form a physiologically tolerable salt.

8. A process for the preparation of a compound as claimed in claim 1 in which Z is NH, comprising a) reacting a benzenesulfonamide of the formula (III),

III or a salt thereof with an iso(thio)cyanate of the formula R(2)-N=C=X, to give a compound of the formula (I), and b) optionally reacting a compound of the formula (I) with a suitable reagent to form a physiologically tolerable salt.

9. A process for the preparation of a compound as claimed in claim 1 in which Z is NH and X is oxygen, comprising a) reacting a benzenesulfonamide of the formula (III)

III or a salt thereof with a trichloroacetamide of the formula Cl$_3$C—CO—NH—R(2), to give a compound of the formula (I), and b) optionally reacting a compound of the formula (I) with a suitable reagent to form a physiologically tolerable salt.

10. A process for the preparation of a compound as claimed in claim 1 in which Z is NH and X is oxygen, comprising a) desulfurizing the corresponding compound of the formula (I) in which Z is NH and X is sulfur on the thiourea group to give a compound of the formula (I), and b) optionally reacting a compound of the formula (I) with a suitable reagent to form a physiologically tolerable salt.

11. A composition, comprising at least one compound as claimed in claim 1 and a carrier.

12. A pharmaceutical composition, comprising an effective amount of at least one compound as claimed in claim 1 and a pharmaceutically tolerable carrier.

13. A pharmaceutical composition for inhibiting ATP-sensitive potassium channels, comprising an effective amount of at least one compound as claimed in claim 1 and a pharmaceutically tolerable carrier.

14. A pharmaceutical composition for stimulating the vagal nervous system, comprising an effective amount of at least one compound as claimed in claim 1 and a pharmaceutically tolerable carrier.

15. A pharmaceutical composition for treating a dysfunction of the autonomic nervous system, wherein the dysfunction affects the heart, comprising an effective amount of at least one compound as claimed in claim 1 and a pharmaceutically tolerable carrier.

16. A pharmaceutical composition for treating a person susceptible to sudden cardiac death, comprising an effective amount of at least one compound as claimed in claim 1 and a pharmaceutically tolerable carrier.

17. A pharmaceutical composition for treating vagal dysfunction in the heart, comprising an effective amount of at least one compound as claimed in claim 1 and a pharmaceutically tolerable carrier.

18. A method of inhibiting ATP-sensitive potassium channels, comprising administering to a patient in need thereof an effective amount of at least one compound as claimed in claim 1.

19. A method of stimulating the vagal nervous system, comprising administering to a patient in need thereof an effective amount of at least one compound as claimed in claim 1.

20. A method of treating a dysfunction of the autonomic nervous system, wherein the dysfunction affects the heart, comprising administering to a patient in need thereof an effective amount of at least one compound as claimed in claim 1.

21. A method of treating a disease, comprising administering to a patient in need thereof an effective amount of at least one compound as claimed in claim 1, wherein the disease is chosen from cardiovascular diseases, ischemic conditions of the heart, coronary heart disease, weakened myocardial contractile force, angina pectoris, cardiac insufficiency, cardiomyopathies, cardiac hypertrophy, and cardiac arrhythmias.

22. A method of treating a person susceptible to sudden cardiac death, comprising administering to a patient in need thereof an effective amount of at least one compound as claimed in claim 1.

23. A method according to claim 22, wherein the patient is a post infarct patient.

24. A method of improving cardiac function, comprising administering to a patient in need thereof an effective amount of at least one compound as claimed in claim 1.

25. A method of treating vagal dysfunction in the heart, comprising administering to a patient in need thereof an effective amount of at least one compound as claimed in claim 1.

* * * * *